United States Patent
Kriheli

(10) Patent No.: US 8,267,127 B2
(45) Date of Patent: Sep. 18, 2012

(54) METHOD AND APPARATUS FOR CONTAMINATION-FREE TRANSFER OF A HAZARDOUS DRUG

(75) Inventor: Marino Kriheli, Tel Aviv (IL)

(73) Assignee: Plastmed, Ltd., Tefen Industrial Park (IL)

( * ) Notice: Subject to any disclaimer, the term of this patent is extended or adjusted under 35 U.S.C. 154(b) by 0 days.

(21) Appl. No.: 13/275,835

(22) Filed: Oct. 18, 2011

(65) Prior Publication Data

US 2012/0046636 A1 Feb. 23, 2012

Related U.S. Application Data

(62) Division of application No. 12/158,719, filed as application No. PCT/IL2008/000550 on Apr. 27, 2008.

(30) Foreign Application Priority Data

Apr. 23, 2007 (IL) .......................... 182743
Feb. 18, 2008 (IL) .......................... 189584

(51) Int. Cl.
 *B65B 3/04* (2006.01)
(52) U.S. Cl. ............ 141/1; 141/329; 141/383; 141/330; 604/905; 604/414; 604/415
(58) Field of Classification Search .................. 141/1, 5, 141/18, 25, 290–291, 329–330, 368, 369, 141/371, 383; 604/411, 414, 415, 905
 See application file for complete search history.

(56) References Cited

U.S. PATENT DOCUMENTS

| 3,938,520 | A | * | 2/1976 | Scislowicz et al. | 604/405 |
| 4,296,786 | A | * | 10/1981 | Brignola | 141/309 |
| 4,552,277 | A | * | 11/1985 | Richardson et al. | 215/249 |
| 4,564,054 | A | * | 1/1986 | Gustavsson | 141/329 |
| 4,576,211 | A | * | 3/1986 | Valentini et al. | 141/329 |
| 4,768,568 | A | * | 9/1988 | Fournier et al. | 141/286 |
| 4,872,494 | A | * | 10/1989 | Coccia | 141/383 |
| 6,604,561 | B2 | * | 8/2003 | Py | 141/329 |
| 6,715,520 | B2 | | 4/2004 | Andreasson et al. | |
| 7,086,431 | B2 | * | 8/2006 | D'Antonio et al. | 141/330 |
| 7,140,401 | B2 | * | 11/2006 | Wilcox et al. | 141/2 |
| 7,744,581 | B2 | * | 6/2010 | Wallen et al. | 604/414 |
| 7,810,529 | B2 | * | 10/2010 | Py | 141/329 |
| 7,975,733 | B2 | * | 7/2011 | Horppu et al. | 141/330 |
| 2009/0069783 | A1 | * | 3/2009 | Ellstrom et al. | 604/415 |
| 2010/0084041 | A1 | * | 4/2010 | Fehr et al. | 141/1 |

FOREIGN PATENT DOCUMENTS

| EP | 0311787 | 4/1989 |
| EP | 0126718 | 11/1994 |
| EP | 1323403 | 7/2003 |
| FR | 2560049 | 8/1985 |
| FR | 2815328 | 4/2002 |
| WO | 0211794 | 2/2002 |
| WO | 03086529 | 10/2003 |
| WO | 2005041846 | 5/2005 |

* cited by examiner

*Primary Examiner* — Timothy L Maust
*Assistant Examiner* — Timothy Kelly
(74) *Attorney, Agent, or Firm* — Roach Brown McCarthy & Gruber, P.C.; Kevin D. McCarthy

(57) ABSTRACT

A method for contamination-free transfer of liquid from one container to another, and devices to carry out the method are disclosed. Contamination-free transfer means that during the transfer process there is no (1) leakage of (a) the liquid, (b) air contaminated by the liquid, and (c) vapor from the liquid to the surroundings, and (2) surrounding contaminants from outside the containers that contact the liquid. The method's advantages include its simplicity, and the contamination-free transfer as defined above. The devices are adapted to effect contamination-free transfer of a hazardous drug to and from any container equipped with a standard connector port.

7 Claims, 23 Drawing Sheets

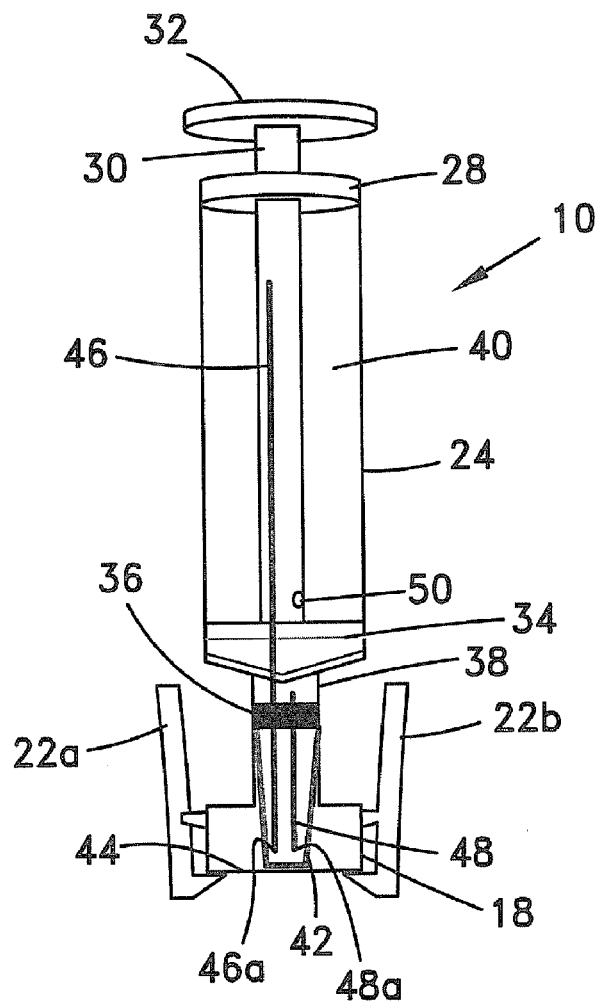
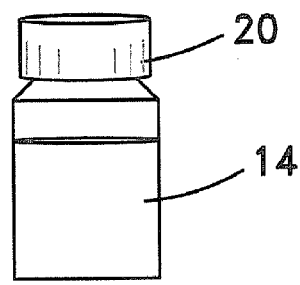
Fig. 2

METHOD AND APPARATUS FOR CONTAMINATION-FREE TRANSFER OF A HAZARDOUS DRUG

CLAIM OF PRIORITY

This application claims priority as a divisional of U.S. patent application Ser. No. 12/158,719, filed on Jun. 23, 2008, which claims priority as a 371 of international PCT/IL2008/000550, filed on Apr. 27, 2008; which further claims priority to Israeli patent application serial number 182743, filed on Apr. 23, 2007 and Israeli patent application serial number 189584, filed on Feb. 18, 2008.

FIELD OF THE INVENTION

The present invention relates to the field of fluid transfer devices. More particularly, the invention relates to an apparatus and method for the contamination-free transfer of a hazardous drug from one container to another.

BACKGROUND OF THE INVENTION

Medical and pharmacological personnel that are involved in the preparation and administration of hazardous drugs suffer the risk of being exposed to drugs and to their vapors, which may escape to the surroundings. As referred to herein, a "hazardous drug" is any injectable material the contact with which, or with the vapors of which, may constitute a health hazard. Illustrative and non-limitative examples of such drugs include, inter alia, cytotoxins, antiviral drugs, chemotherapy drugs, antibiotics, and radiopharmaceuticals, such as herceptin, cisplatinum, fluorouracil, leucovorin, taxol, metatroxat, gemzar, cyclophosphamide, cytoxan, and neosar, or a combination thereof, in a liquid, solid, or gaseous state.

Hazardous drugs in liquid or powder form are contained within vials, and are typically prepared in a separate room by pharmacists provided with protective clothing, a mouth mask, and a laminar flow safety cabinet. A syringe provided with a cannula, i.e. a hollow needle, is used for transferring the drug from a vial. After being prepared, the hazardous drug is added to a solution contained in a bag which is intended for parenteral administration, such as a saline solution intended for intravenous administration.

Since hazardous drugs are toxic, direct bodily contact thereto, or exposure to even micro-quantities of the drug vapors, considerably increases the risk of developing health fatalities such as skin cancer, leukemia, liver damage, malformation, miscarriage and premature birth. Such exposure can take place when a drug containing receptacle, such as a vial, bottle, syringe, and intravenous bag, is subjected to overpressure, resulting in the leakage of fluid or air contaminated by the hazardous drug to the surroundings. Exposure to a hazardous drug also results from a drug solution remaining on a needle tip, on a vial or intravenous bag seal, or by the accidental puncturing of the skin by the needle tip.

Some prior art liquid transfer devices are intended to provide contamination-free transfer of hazardous drugs.

For example, WO 2005/041846 discloses a drug mixing system comprising a receptacle port adaptor adapted to be inserted into a port of a fluid receptacle, a vial adaptor adapted for connection to a vial containing a drug, and a syringe adaptor attached to a syringe. The syringe adaptor is adapted to be brought into fluid communication and mechanically locked to at least one of the receptacle port adaptor and vial adaptor in an axial motion. When a user retracts the syringe plunger, fluid flows directly into the syringe, ensuring that the fluid remains sterile and that the user is not exposed to the fluid. The user is also not exposed to the fluid as the syringe adaptor is connected to, or disconnected from, the receptacle port adaptor or vial adaptor since the septum of the syringe adaptor is pushed into touching engagement with the corresponding septum of the receptacle port adaptor or vial adaptor, thereby preventing exposure of the syringe needle to the environment. The syringe adaptor comprises a septa housing, a compression spring seated within the septa housing, and a needle sealingly mounted within the housing and axially extending within the spring. The septa housing is movable relative to the needle in order to expose the needle tip.

This drug transfer system is an open system, which comprises a membrane vent and filter, for venting at least one of the receptacle port adaptor, the vial adaptor, and syringe adaptor to the atmosphere. After filtration, air contaminated by micro-quantities of the drug vapors is nevertheless exposed to the environment. Another disadvantage of this drug mixing system is that two septa are placed in mutual touching engagement by means of the biasing force of the spring. The biasing force applied by the spring is lower when the two septa are first placed in contact and increases as the septa are pierced by the needle. Consequently, any inadvertent movement of the system when the two septa are first placed in contact is liable to cause the two septa to be separated from each other and to cause a risk of exposure of the dangerous drug to the surroundings. An additional disadvantage of this system is that a securing device is engaged when the spring is fully compressed, and a release mechanism for manually disengaging the securing device is needed. In addition the system of the invention comprises a venting filter, which vents air that might be contaminated by vapors of the drug to the environment.

It would be desirable to provide a connector that causes two separated septa to be brought in locking engagement prior to a liquid transfer operation and to be separated following said operation without having to set a securing device or a release mechanism.

WO 02/11794, WO 03/086529, and U.S. Pat. No. 6,715,520 disclose a closed-system fluid transfer assembly for contamination-free drug transfer, i.e. without passage of a gas from the interior of a receptacle containing a hazardous drug to the surrounding environment. A connector to a drug bottle has a hollow needle for penetrating the closure of the drug bottle at a predetermined angle when establishing a fluid transfer line in a fluid transfer assembly. A connector locking member and membrane are included in a double membrane bayonet coupling with the fluid transfer device. A gas channel within the hollow needle transports gas from the bottle to a flexible container constituting a pressure compensator, and vice versa. The fluid transfer device comprises a syringe and a coupling unit. The coupling unit has a first part arranged for connection to the syringe and a second part arranged for connection to the drug bottle connector. The second part, which can be telescoped into the first part, is prevented from rising by a detent which slips into an opening of the first part and its locked position is released by an outwardly displaceable handle connected to the detent. After the drug is received in the fluid transfer device, an injection needle of the coupling unit penetrates a membrane of the injection port of a mixing device connected to the inlet port of an infusion bag. A spike member of an infusion line pierces the membrane of an outlet port of the mixing device without leakage.

This fluid transfer assembly requires a large number of steps in order to establish a connection by which a hazardous drug is transferred, including the steps of connecting the connector to the drug bottle, rotating and locking the coupling unit onto the syringe, lowering the coupling unit onto the connector, rotating and locking the coupling unit onto the connector, outwardly displacing the handle of the coupling unit, pressing on the fluid transfer assembly in order to retract the second part into the first part of the coupling unit, and manipulating the syringe. An additional disadvantage of this fluid transfer assembly is that a predetermined volume of air needs to be injected to the flexible container prior to a liquid transfer operation, in order to displace a corresponding volume of the drug from the vial; however, the volume of drug to be transferred, which is dependent on the volume of the injected air, cannot be adjusted by the health practitioner during a liquid transfer operation. An additional disadvantage of this fluid transfer assembly is that the air that needs to be injected prior to operation is taken from the environment and therefore involves the risk of introducing contaminants from the environment to the drug and violating its sterility.

Also, there is a risk that the flexible container, which is made of sheet material and is located externally to the syringe, may be punctured, thereby exposing the contaminated air to the environment and rendering the fluid transfer assembly inoperable. Furthermore, the sharp hollow needle of the drug bottle connector endangers, while remaining exposed to, a pharmacist until it penetrates the drug bottle closure. Consequently, this fluid transfer assembly cannot be considered within the group of safety products generally referred to as "needleless", i.e. a transfer device having a sharp needle which is not exposed to a user. An additional disadvantage of this fluid transfer assembly is that an operator is liable to forget to perform one or more steps during the connection sequence, leading to the dangerous result that a double membrane seal will not be established. The dangerous drug will therefore be exposed to the surrounding air or is liable to be discharged from the syringe, thereby endangering the operator and bystanders.

It is an object of the present invention to provide a closed-system fluid transfer assembly that is adapted to prevent the leakage of a hazardous drug or air contaminated by the hazardous drug or drug vapors and prevents contaminants from the environment from coming into contact with the drug during the transfer process.

It is another object of the present invention to provide a closed-system fluid transfer assembly in which the same volume of the hazardous drug and air are exchanged internally by means of a pressure equalization arrangement within the fluid transfer assembly, thereby preventing any exposure of a user to the hazardous drug.

It is yet an additional object of the present invention to provide a fluid transfer assembly which does not expose any sharp objects such as the tip of a needle to a user during any stage of a fluid transfer operation.

Other objects and advantages of the invention will become apparent as the description proceeds.

SUMMARY OF THE INVENTION

As referred to herein, the term "exchange" means the transfer of first and second fluids in opposite directions within different fluid passageways between two containers such that when the first fluid is transferred from the first container to the second container an equal volume of the second fluid is transferred from the second container, to the first container.

As referred to herein, the term "contamination-free transfer of liquid" means that during the transfer process there is no leakage of the liquid or air contaminated by the liquid or vapors of the liquid to the surroundings and also that no contaminants from the surroundings come into contact with the liquid.

A "fluid passageway" means a flow path between said syringe means and said receptacle, which comprises at least one segment from each of said syringe means and said receptacle that are in mutual fluid communication when said syringe means is coupled to said receptacle.

A "segment" means a volume enclosed by one or more walls in which a fluid can flow.

As referred to herein, "proximal" means in a direction closer to a user who manipulates the apparatus.

As referred to herein, "distal" means in a direction farther from a user who manipulates the apparatus.

As referred to herein, a "secured double engagement procedure" means a procedure during which two pierceable membranes of two fluid transfer components, respectively, are brought to mutual engagement and during which separation of said two membranes is prevented during the application of a distally directed force.

As referred to herein, fluid transfer component means any component, e.g. syringe, vial, infusion bag, adaptors of various types, that are used to contain, transport, and transfer a liquid drug from one fluid transfer component to another or to a patient.

In a first aspect the invention is a method for the contamination-free transfer of liquid from a first container containing a volume of the liquid and at least an equal volume of gas to a second container containing at least a volume of gas equal to the amount of liquid that is to be transferred into it. The method of the invention comprises the following steps:

a) providing a fluid transfer device comprising: a closed container having a moveable internal partition that divides the interior of the container into two separate fluid tight chambers having variable volume, wherein one of the chambers is a gas chamber and the other of the chambers is a liquid chamber; a first segment of a gas channel and a first segment of a liquid channel, wherein the proximal ends of the first segments are in fluid communication with the interiors of the gas chamber and the liquid chamber respectively and the distal ends of the first segments are closed by sealing means;

b) providing a second segment of a gas channel and a second segment of a liquid chamber, wherein the distal ends of the second segments are in fluid communication with the interior of the first container and the proximal ends of the second segments are closed by sealing means;

c) pushing the distal end of the first segments in the direction of the proximal end of the second segments until the distal ends of the first segments penetrate the sealing means at the distal end of the first segments, penetrate the sealing means at the proximal end of the second segments, and enter the proximal ends of the second segments, thereby providing a continuous gas channel between the interior of the first container and the interior of the gas chamber and a separate continuous liquid channel between the interior of the first container and the interior of the liquid chamber;

d) allowing an equilibrium to be established between the pressure of the gas in the first container and the pressure of the gas in the gas chamber and between the pressure exerted on the liquid in the first container and the pressure exerted on the liquid in the liquid chamber;

e) moving the internal partition in a first direction in order to increase the volume of the liquid chamber and instantaneously decrease the pressure inside the liquid chamber and simultaneously decrease the volume of the gas chamber and instantaneously increase the pressure of the gas inside the gas chamber, wherein the differences of pressure caused by moving the internal partition cause liquid to flow from the first container through the continuous liquid channel into the liquid chamber and an equal volume of gas to flow simultaneously from the gas chamber through the continuous air channel into the first container, wherein the flow of liquid in one direction and simultaneous flow of gas in the other direction continues until the internal partition stops moving and the equilibrium is reestablished;

f) disconnecting the first container from the fluid transfer device by pulling the distal ends of the first segments back out of the proximal ends of the second segments, through the sealing means at the proximal end of the second segments, thereby enclosing the ends of the second segments, and through the sealing means at the distal end of the first segments, thereby enclosing the ends of the first segments;

g) providing a third segment of a gas channel and a third segment of a liquid channel, wherein the distal ends of the third segments are in fluid communication with the interior of the second container and the proximal ends of the third segments are closed by sealing means;

h) pushing the distal end of the first segments in the direction of the proximal end of the third segments until the distal ends of the first segments penetrate the sealing means at the distal end of the first segments, penetrate the sealing means at the proximal end of the third segments, and enter the proximal ends of the third segments, thereby providing a continuous gas channel between the interior of the second container and the interior of the gas chamber and a separate continuous liquid channel between the interior of the second container and the interior of the liquid chamber;

i) allowing an equilibrium to be established between the pressure of the gas in the second container and the pressure of the gas in the gas chamber and between the pressure exerted on the liquid in the second container and the pressure exerted on the liquid in the liquid chamber;

j) moving the internal partition in a second direction in order to decrease the volume of the liquid chamber and instantaneously increase the pressure inside the liquid chamber and simultaneously increase the volume of the gas chamber and instantaneously decrease the pressure of the gas inside the gas chamber, wherein the differences of pressure caused by moving the internal partition cause liquid to flow from the liquid chamber through the continuous liquid channel into the second container and an equal volume of gas to flow simultaneously from the second container through the continuous air channel into the gas chamber, wherein the flow of liquid in one direction and simultaneous flow of gas in the other direction continues until the internal partition stops moving and the equilibrium is reestablished; and k) disconnecting the second container from the fluid transfer device by pulling the distal ends of the first segments back out of the proximal ends of the third segments, through the sealing means at the proximal end of the third segments, thereby closing the ends of the third segments, and through the sealing means at the distal end of the first segments, thereby enclosing the ends of the first segments;

The method is characterized in that all of the liquid and the gas that flows between the fluid transfer device and the first container was present in either the fluid transfer device or the first container before the continuous liquid and gas channels between them were provided and all of the liquid and the gas that flows between the fluid transfer device and the second container was present in either the fluid transfer device or the second container before the continuous liquid and gas channels between them were provided.

If the second container does not contain a volume of gas that is at least equal to the volume of liquid to be transferred, then the method is modified by not providing means to place the gas chamber in fluid communication with the interior of the second container. Instead the distal end of the third segment of gas channel is connected to a one-way valve, thereby allowing filtered air from the surroundings to flow into the gas chamber as the liquid flows from the liquid chamber into the second container.

A specific application in which the method of the invention can be used is for the transfer of a hazardous drug from one container to another.

In another aspect the invention is a fluid transfer apparatus for carrying out the method of the first aspect. The apparatus comprises: syringe means, means for releasably coupling the syringe means to a container in which a liquid is storable, and fluid exchange means adapted to allow equalization of the gas pressure within the syringe means to the gas pressure within the container and to allow exchange of a desired volume of the liquid between the container and the syringe means.

One embodiment of the fluid transfer apparatus of the invention comprises:

a) a syringe-like proximal section comprising:
   i) a cylindrical body;
   ii) a tubular throat;
   iii) a separating element that prevents the passage of fluids between the connector section and the throat; and
   iv) a piston that is displaceable within the cylindrical body, the piston defining a distal liquid chamber and a proximal gas chamber, both of variable volume;

b) a connector section fixedly attached to the distal end of the throat of the proximal section, wherein the distal end of the connector section is adapted to be connectable to a fluid transfer component;

c) a liquid conduit that passes through and is rigidly attached to the separating element, wherein the distal end of the liquid conduit begins in the connector section and the proximal end of the liquid conduit terminates in the liquid chamber;

d) a gas conduit that passes through and is rigidly attached to the separating element, wherein the distal end of the gas conduit begins in the connector section and the proximal end of the gas conduit terminates in the gas chamber; and e) a membrane located at the distal end of the connector section, wherein the membrane encloses the distal ends of the liquid conduit and the air conduit isolating them from the surroundings.

The connector section is configured to allow the head portion of the fluid transfer component to enter the interior of the connector section and to allow the membrane in the connector section to be pushed proximally when it is contacted by a membrane located in the head portion of the fluid transfer component. Further pushing of the membranes together causes the distal ends of the liquid conduit and the air conduit to penetrate the membrane in the connector section and the central seal in the head portion, thereby establishing an open liquid channel via the liquid conduit between the interior of the liquid chamber and the interior of the fluid transfer component and a separate open air channel via the air conduit between the interior of the air chamber and the interior of the fluid transfer component.

In embodiments of the apparatus of the invention the connector section comprises a distal collar formed integrally with, or connected to the throat and suitably sized to surround the head portion of the fluid transfer component, and locking elements connected to the collar and adapted to releasably engage the distal edge of the head portion of the fluid transfer component.

In these embodiments the membrane located at the distal end of the connector section can be a deformable membrane having the shape of a truncated cone, which is firmly attached at its base to the separating element and distally extends to the distal end of the distal collar. Safety means can be provided for preventing deformation of the membrane.

These embodiments of the apparatus of the invention can be connected to a fluid transfer component in order to affect a secured double membrane engagement by carrying out the following steps:
- a) Position the head portion of the fluid transfer component close to the distal collar.
- b) Move the head portion and the distal collar axially closer together until the membrane located in the head portion contacts the deformable membrane in the connector section.
- c) Continue to move the head portion and the distal collar axially closer together compressing the deformable membrane in the connector section until the distal ends of the liquid and air conduits penetrate through both of the membranes.
- d) Continue to move the head portion and the distal collar axially closer until the locking elements connected to the collar releasably engage the distal edge of the head portion.

The steps described above for coupling the connector section of the liquid transfer device to the liquid transfer component can be, and preferably are, carried out using one axial motion.

In other embodiments of the apparatus of the invention the connector section comprises a hollow cylindrical outer body. The hollow cylindrical outer body has:
- a. a distal shoulder portion radially protruding from the outer body and terminating with an opening through which the proximal end of a fluid transfer component can be inserted for coupling;
- b. a closed proximal cap having a central portion comprising connection means protruding proximally from it to connect to the distal end of the syringe-like proximal portion of the apparatus;
- c. a needle holder protruding into the interior of the outer body from a central portion of the closed proximal cap for retaining therein two conduits comprising sharp pointed ends and further provided with apertures through which liquid and gas respectively are transferred during a fluid transfer operation; and
- d. a double membrane seal actuator reciprocably displaceable within the hollow interior of the outer body.

The double membrane seal actuator comprises:
- a. a cylindrical actuator casing;
- b. a proximal membrane that seals the proximal end of the casing
- c. a distal membrane that seals the distal end of the casing, wherein a part of the distal membrane protrudes distally from the casing; and
- d. at least two resilient arms which are connected at a proximal end thereof to an intermediate portion of the exterior of the casing and comprise enlarged elements at their distal ends.

When the double membrane seal actuator is at the distal end of the cylindrical body of the connector section the enlarged elements of the resilient arms are pressed into the distal shoulder portion of the cylindrical body of the connector section, thereby allowing the membrane enclosure at the proximal end of a fluid transfer component to be inserted into the opening at the distal end of the connector section and advanced until the membrane in the membrane enclosure contacts the part of the distal membrane that protrudes distally from the casing of the double membrane seal actuator.

The diameter of the distal shoulder portion and the size of the enlarged elements at the distal end of the arms are such that, when an axial force is applied to push the double membrane seal actuator and fluid transfer component towards each other, the sides of the membrane enclosure prevent the enlarged elements at the distal end of the arms from moving radially inwards. This causes the distal actuator membrane to be compressed against the membrane in the membrane enclosure until the sides of the membrane enclosure are displaced proximally in relation to the enlarged elements. At this point the enlarged elements have room to move radially inwards, are released from the distal shoulder portion of the double membrane seal actuator, and abut the distal underside of the membrane enclosure. In this way the distal actuator membrane is locked against the membrane in the membrane enclosure in secured and compressed engagement, preventing disengagement of the actuator from the fluid transfer component, and allowing the actuator and the coupled fluid transfer component to be reciprocally displaced within the hollow interior of the outer body of the connector section.

The distance that the actuator and attached fluid transfer component can be displaced proximally within the hollow interior of the outer body of the connector section and the length of the two conduits are such that, when the actuator and the attached fluid transfer component are displaced proximally, the sharp pointed ends of the two conduits penetrate the distal membrane of the actuator and the membrane in the membrane enclosure, thereby establishing a liquid path and a gas path respectively between the connector section and the fluid transfer component. When the actuator and attached fluid transfer component are displaced distally within the hollow interior of the outer body of the connector section, the sharp pointed ends of the two conduits are pulled back through the distal membrane of the actuator and the membrane in the membrane enclosure, thereby breaking the liquid path and the gas path respectively between the connector section and the fluid transfer component.

When the double membrane seal actuator is at the distal end of the cylindrical body of the conductor section, the sharp pointed ends of the two conduits are located between the proximal membrane and the distal membrane of the double membrane seal actuator.

The embodiments of the apparatus of the invention just described can be coupled to a fluid transfer component in order to affect a secured double membrane engagement by carrying out the following steps:
- a. Position the opening in the distal shoulder portion of the outer body of the connector section in the vicinity of the proximal end of the fluid transfer component.
- b. Initiate a double membrane engagement operation by distally displacing the outer body of the connector section until the membrane enclosure at the proximal end of the fluid transfer component is received in the interior of the connector section.

c. Additionally displace distally the outer body relative to the fluid transfer component until the distal membrane of the actuator contacts and is pressed against the membrane in the membrane enclosure at the proximal end of the fluid transfer component. During this step the enlarged elements at the distal end of the arms attached to the double membrane seal actuator are held in the distal shoulder portion of the outer body of the connector section by the sides of the membrane enclosure. This prevents the actuator from moving proximally within the outer body of the connector section. and d. Additionally displace distally the outer body relative to the fluid transfer component until the distal membrane of the actuator and the membrane in the membrane enclosure at the proximal end of the second fluid transfer component are compressed together sufficiently to allow the sides of the membrane enclosure to pass the enlarged elements. This allows the arms to move radially inwards, thereby locking the distal actuator membrane against the membrane in the membrane enclosure in secured and compressed engagement, preventing disengagement of the actuator from the fluid transfer component, and allowing the actuator and the attached fluid transfer component to be reciprocably displaced within the hollow interior of the outer body of the connector section. When the actuator and attached fluid transfer component are displaced proximally within the hollow interior of the outer body of the connector section, the sharp pointed ends of the two conduits penetrate the distal membrane of the actuator and the membrane in the membrane enclosure, thereby establishing separate liquid and gas paths between the connector section and the fluid transfer component. When the actuator and attached fluid transfer component are displaced distally within the hollow interior of the outer body of the connector section, the sharp pointed ends of the two conduits are pulled back through the distal membrane of the actuator and the membrane in the membrane enclosure, thereby breaking the liquid and gas paths between the connector section and the fluid transfer component.

The structure of the connector section enables the connector section and the fluid transfer components to be connected by a single axial motion and disconnected by a single axial motion without having to set a locking securing device or a release mechanism.

In another aspect, the invention is a connector section for use in a fluid transfer operation. The connector section comprises a hollow cylindrical outer body having:

a. a distal shoulder portion radially protruding from the outer body and terminating with an opening through which the proximal end of a fluid transfer component can be inserted for coupling;

b. a closed proximal cap having a central portion comprising connection means protruding proximally from it to connect to the distal end of a fluid transfer apparatus;

c. a needle holder protruding into the interior of the outer body from a central portion of the closed proximal cap for retaining therein at least one conduit comprising a sharp pointed end and further provided with apertures through which fluid is transferred during the fluid transfer operation; and d. a double membrane seal actuator reciprocably displaceable within the hollow interior of the outer body.

The double membrane seal actuator comprises:

a. a cylindrical actuator casing;

b. a proximal membrane that seals the proximal end of the casing c. a distal membrane that seals the distal end of the casing, wherein a part of the distal membrane protrudes distally from the casing; and d. at least two resilient arms which are connected at a proximal end thereof to an intermediate portion of the exterior of the casing and comprise enlarged elements at their distal ends.

When the double membrane seal actuator is at the distal end of the cylindrical body of the connector section the enlarged elements of the resilient arms are pressed into the distal shoulder portion of the cylindrical body of the connector section, thereby allowing the membrane enclosure at the proximal end of a fluid transfer component to be inserted into the opening at the distal end of the connector section and advanced until the membrane in the membrane enclosure contacts the part of the distal membrane that protrudes distally from the casing of the double membrane seal actuator.

The diameter of the distal shoulder portion and the size of the enlarged elements at the distal end of the arms are such that, when an axial force is applied to push the double membrane seal actuator and fluid transfer component towards each other, the sides of the membrane enclosure prevent the enlarged elements at the distal end of the arms from moving radially inwards. This causes the distal actuator membrane to be compressed against the membrane in the membrane enclosure until the sides of the membrane enclosure are displaced proximally in relation to the enlarged elements. At this point the enlarged elements have room to move radially inwards, are released from the distal shoulder portion of the double membrane seal actuator, and abut the distal underside of the membrane enclosure. In this way the distal actuator membrane is locked against the membrane in the membrane enclosure in secured and compressed engagement, preventing disengagement of the actuator from the fluid transfer component, and allowing the actuator and the coupled fluid transfer component to be reciprocably displaced within the hollow interior of the outer body of the connector section.

The distance that the actuator and attached fluid transfer component can be displaced proximally within the hollow interior of the outer body of the connector section and the length of the two conduits are such that, when the actuator and the attached fluid transfer component are displaced proximally, the sharp pointed ends of the two conduits penetrate the distal membrane of the actuator and the membrane in the membrane enclosure, thereby establishing a liquid path and a gas path respectively between the connector section and the fluid transfer component. When the actuator and attached fluid transfer component are displaced distally within the hollow interior of the outer body of the connector section, the sharp pointed ends of the two conduits are pulled back through the distal membrane of the actuator and the membrane in the membrane enclosure, thereby breaking the liquid path and the gas path respectively between the connector section and the fluid transfer component.

When the double membrane seal actuator is at the distal end of the cylindrical body of the conductor section, the sharp pointed ends of the two conduits are located between the proximal membrane and the distal membrane of the double membrane seal actuator.

The connector section of the invention can be coupled to a fluid transfer component in order to affect a secured double membrane engagement by carrying out the following steps:

a. Position the opening in the distal shoulder portion of the outer body of the connector section in the vicinity of the proximal end of the fluid transfer component.
b. Initiate a double membrane engagement operation by distally displacing the outer body of the connector section until the membrane enclosure at the proximal end of the fluid transfer component is received in the interior of the connector section.
c. Additionally displace distally the outer body relative to the fluid transfer component until the distal membrane of the actuator contacts and is pressed against the membrane in the membrane enclosure at the proximal end of the fluid transfer component. During this step the enlarged elements at the distal end of the arms attached to the double membrane seal actuator are held in the distal shoulder portion of the outer body of the connector section by the sides of the membrane enclosure, thereby preventing the actuator from moving proximally within the outer body of the connector section. and
d. Additionally displacing distally the outer body relative to the fluid transfer component until the distal membrane of the actuator and the membrane in the membrane enclosure at the proximal end of the second fluid transfer component are compressed together sufficiently to allow the sides of the membrane enclosure to pass the enlarged elements. This allows the arms to move radially inwards, thereby locking the distal actuator membrane against the membrane in the membrane enclosure in secured and compressed engagement, preventing disengagement of the actuator from the fluid transfer component, and allowing the actuator and the attached fluid transfer component to be reciprocably displaced within the hollow interior of the outer body of the connector section. When the actuator and attached fluid transfer component are displaced proximally within the hollow interior of the outer body of the connector section, the sharp pointed ends of the two conduits penetrate the distal membrane of the actuator and the membrane in the membrane enclosure, thereby establishing separate liquid and gas paths between the connector section and the fluid transfer component. When the actuator and attached fluid transfer component are displaced distally within the hollow interior of the outer body of the connector section, the sharp pointed ends of the two conduits are pulled back through the distal membrane of the actuator and the membrane in the membrane enclosure, thereby breaking the liquid and gas paths between the connector section and the fluid transfer component.

The structure of the connector section enables the connector section and the fluid transfer components to be connected by a single axial motion and disconnected by a single axial motion without having to set a locking securing device or a release mechanism.

BRIEF DESCRIPTION OF THE DRAWINGS

In the drawings:

FIG. 2 is a schematic vertical cross sectional view of the apparatus of FIG. 1;

DETAILED DESCRIPTION OF PREFERRED EMBODIMENTS

Figure 1:
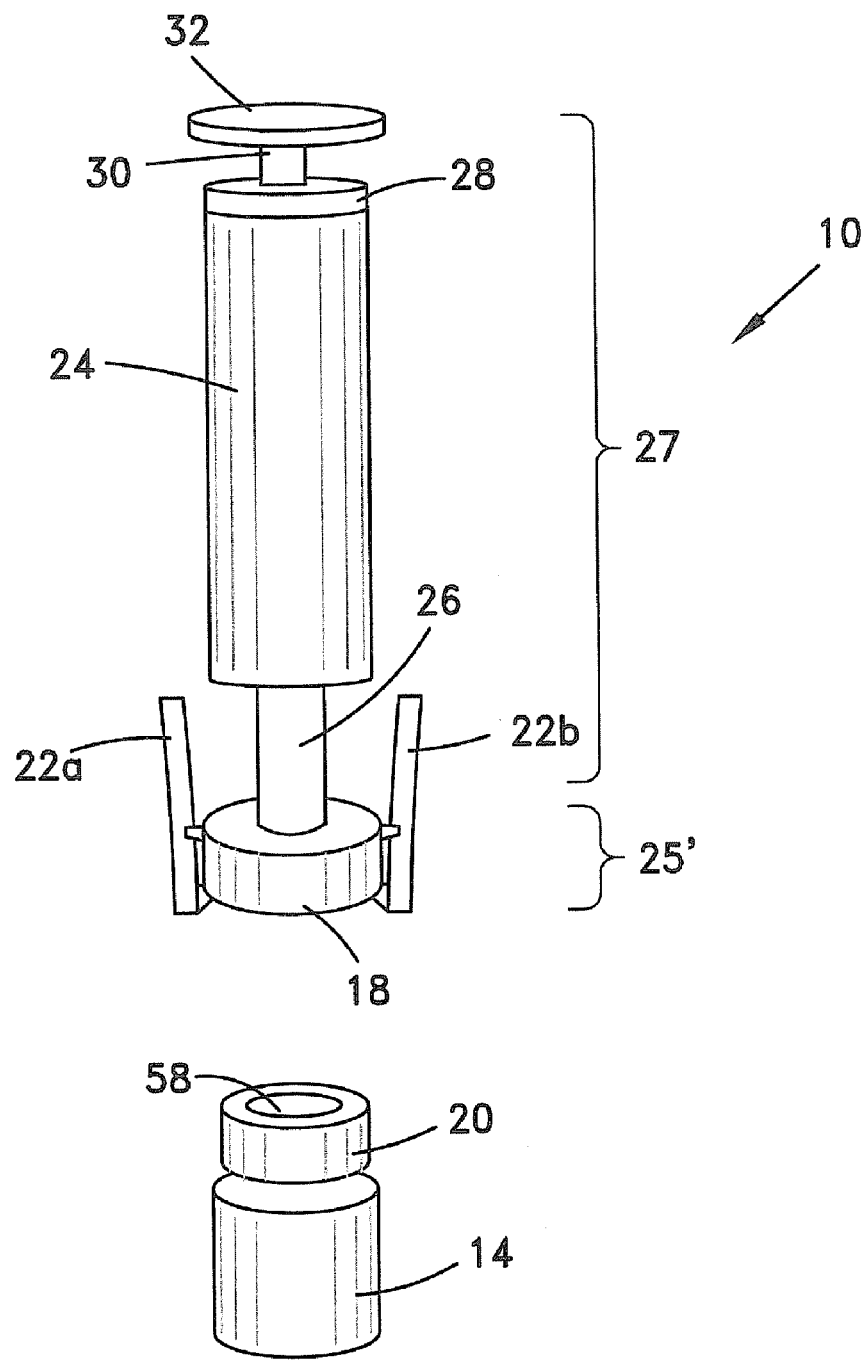
FIG. 1 is a perspective view from the side of an apparatus for transferring hazardous drugs, according to one embodiment of the invention.

The invention is a method that allows contamination-free transfer of a liquid from one container to another and devices including embodiments of a transfer apparatus and adaptors that are used to carry out the method. The main advantages of the method, in addition to its simplicity, is that at no stage of the transfer procedure is there leakage of the liquid or air contaminated by the liquid or vapors of the liquid to the surroundings and also that no contaminants from the surroundings come into contact with the liquid.

Although the method is described herein as transferring a liquid from one container to a second one, it is to be understood that the transfer can take place between several containers. For example, liquid can be withdraw from a first container and then part of it injected into five different containers, following which part of the liquid can be withdraw from one of the container and then injected into the original container and so on, in practically any order and combination and quantity.

The present invention is particularly directed towards providing an apparatus that is adapted to effect contamination-free transfer of a hazardous drug to and from any container equipped with a standard connector port.

The method of the invention for the contamination-free transfer of liquid from a first container containing a volume of the liquid and at least an equal volume of gas to a second container containing at least a volume of gas equal to the amount of liquid that is to be transferred into it comprises the following steps:

a) providing a fluid transfer apparatus comprising: a closed container having a moveable internal partition that divides the interior of the container into two separate fluid tight chambers having variable volume, wherein one of the chambers is a gas chamber and the other of the chambers is a liquid chamber; a first segment of a gas channel and a first segment of a liquid channel, wherein the proximal ends of the first segments are in fluid communication with the interiors of the gas chamber and the liquid chamber respectively and the distal ends of the first segments are enclosed by sealing means;

b) providing a second segment of a gas channel and a second segment of a liquid chamber, wherein the distal ends of the second segments are in fluid communication with the interior of the first container and the proximal ends of the second segments are enclosed by sealing means;

c) pushing the distal end of the first segments in the direction of the proximal end of the second segments until the distal ends of the first segments penetrate the sealing means at the distal end of the first segments, penetrate the sealing means at the proximal end of the second segments, and enter the proximal ends of the second segments, thereby providing a continuous gas channel between the interior of the first container and the interior of the gas chamber and a separate continuous liquid channel between the interior of the first container and the interior of the liquid chamber;

d) allowing an equilibrium to be established between the pressure of the gas in the first container and the pressure of the gas in the gas chamber and between the pressure exerted on the liquid in the first container and the pressure exerted on the liquid in the liquid chamber;

e) moving the internal partition in a first direction in order to increase the volume of the liquid chamber and instantaneously decrease the pressure inside the liquid chamber and simultaneously decrease the volume of the gas chamber and instantaneously increase the pressure of the gas inside the gas chamber, wherein the differences of pressure caused by moving the internal partition cause liquid to flow from the first container through the continuous liquid channel into the liquid chamber and an equal volume of gas to flow simultaneously from the gas chamber through the continuous air channel into the first container, wherein the flow of liquid in one direction and simultaneous flow of gas in the other direction continues until the internal partition stops moving and the equilibrium is reestablished;

f) disconnecting the first container from the fluid transfer device by pulling the distal ends of the first segments back out of the proximal ends of the second segments, through the sealing means at the proximal end of the second segments, thereby enclosing the ends of the second segments, and through the sealing means at the distal end of the first segments, thereby enclosing the ends of the first segments;

g) providing a third segment of a gas channel and a third segment of a liquid channel, wherein the distal ends of the third segments are in fluid communication with the interior of the second container and the proximal ends of the third segments are enclosed by sealing means;

h) pushing the distal end of the first segments in the direction of the proximal end of the third segments until the distal ends of the first segments penetrate the sealing means at the distal end of the first segments, penetrate the sealing means at the proximal end of the third segments, and enter the proximal ends of the third segments, thereby providing a continuous gas channel between the interior of the second container and the interior of the gas chamber and a separate continuous liquid channel between the interior of the second container and the interior of the liquid chamber;

i) allowing an equilibrium to be established between the pressure of the gas in the second container and the pressure of the gas in the gas chamber and between the pressure exerted on the liquid in the second container and the pressure exerted on the liquid in the liquid chamber;

j) moving the internal partition in a second direction in order to decrease the volume of the liquid chamber and instantaneously increase the pressure inside the liquid chamber and simultaneously increase the volume of the gas chamber and instantaneously decrease the pressure of the gas inside the gas chamber, wherein the differences of pressure caused by moving the internal partition cause liquid to flow from the liquid chamber through the continuous liquid channel into the second container and an equal volume of gas to flow simultaneously from the second container through the continuous air channel into the gas chamber, wherein the flow of liquid in one direction and simultaneous flow of gas in the other direction continues until the internal partition stops moving and the equilibrium is reestablished; and k) disconnecting the second container from the fluid transfer device by pulling the distal ends of the first segments back out of the proximal ends of the third segments, through the sealing means at the proximal end of the third segments, thereby enclosing the ends of the third segments, and through the sealing means at the distal end of the first segments, thereby enclosing the ends of the first segments.

Illustrative embodiments of the devices used to carry out the method are described herein below.

FIG. 1 illustrates a perspective view of an apparatus 10 for transferring hazardous drugs without contaminating the surroundings, according to one embodiment of the invention. The proximal section 27 of apparatus 10 is essentially a conventional syringe, which is adapted to draw a desired volume of a hazardous drug from a fluid transfer component, e.g. a vial 14 or an intravenous (IV) bag in which it is contained and to subsequently transfer the drug to another fluid transfer component.

Connector section 25' of transfer apparatus 10 is shown to comprise integral distal collar 18, which is suitably sized to surround head portion 20 of vial 14, locking elements 22a and 22b for releasably engaging head portion 20 of vial 14 within collar 18. Proximal section 27 of apparatus 10 comprises cylinder 24, tubular throat 26 having a considerably smaller diameter than cylinder 24 and extending from cylinder 24 to collar 18, annular rubber stopper 28 fitted on the proximal end of cylinder 24, hollow piston rod 30 which sealingly passes through stopper 28, and proximal piston rod cap 32 by which a user can push and pull piston rod 30 up and down through stopper 28. Collar 18 and cylinder 24 are made of a rigid material, e.g. plastic.

FIG. 2 illustrates a schematic cross sectional view of transfer apparatus 10. As shown, piston rod 30 extends from cap 32 to piston 34, which sealingly engages the inner wall of, and is displaceable with respect to, cylinder 24. Separating element 36 is internal to, and integrally formed with, throat 26. Piston 34 defines two chambers of variable volume: a distal liquid chamber 38 between the distal face of piston 34 and separating element 36 and a proximal air chamber 40 between the proximal face of piston 34 and stopper 28. A deformable membrane 42 having the shape of a truncated cone is firmly attached at its base to separating element 36 and distally extends to the distal end 44 of collar 18. Membrane 42 completely surrounds two conduits 46 and 48 and, when in its undeformed configuration, membrane 42 serves to effectively isolate the interior of transfer apparatus 10 from the surroundings. Conduits 46 and 48 pass through and are firmly bonded to separating element 36. Distal ends 46a and 48a of conduits 46 and 48, respectively, which are substantially equally spaced from distal end 44 of collar 18, have sharp pointed ends. Elongated conduit 46 is an air conduit and extends through the hollow piston rod 30. Piston rod 30 is formed with a distal aperture 50, so that air, which flows through conduit 46, is able to exit from the interior of piston rod 30 via aperture 50 to air chamber 40. Conduit 48 is a liquid conduit through which a solution of a hazardous drug can flow from vial 14 to transfer apparatus 10 or vice versa. Conduit 48, which is considerably shorter than air conduit 46, terminates within liquid chamber 38.

Figure 3:
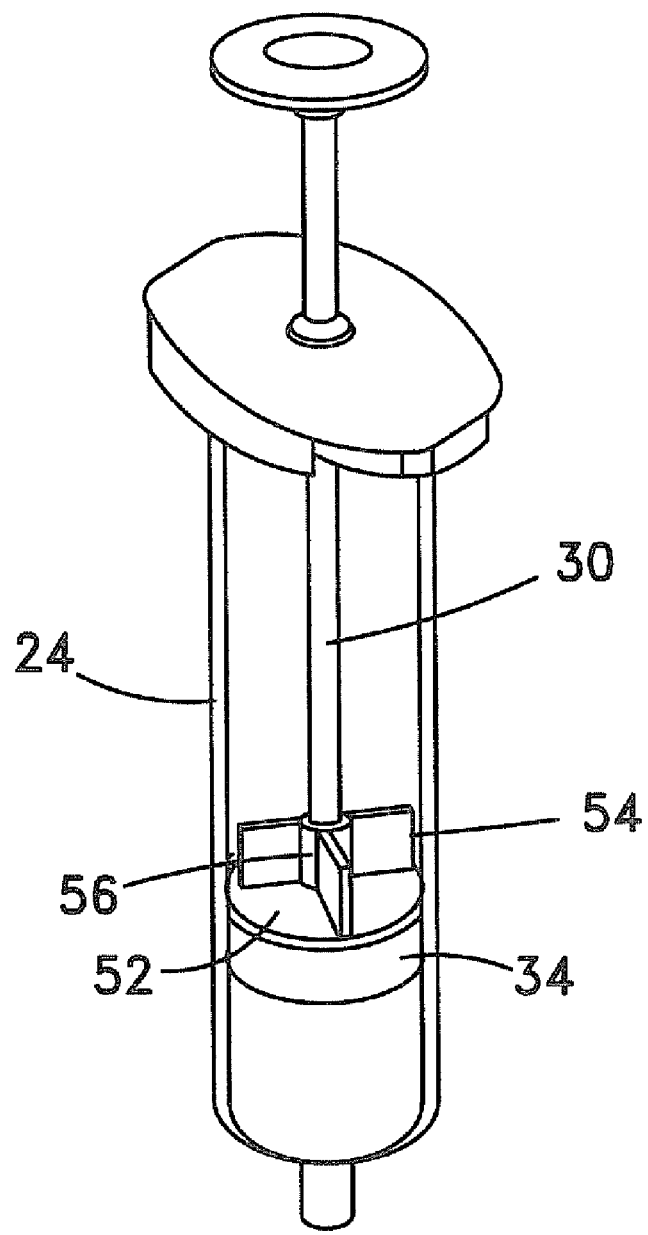
FIG. 3 is a perspective view of ribs for reinforcing the attachment of a hollow piston rod to a piston.

As shown in FIG. 3, hollow piston rod 30 may be attached to piston 34 by means of an annular disc 52, e.g. made of plastic, which is engaged with piston 34. A plurality of reinforcing ribs 54 are attached to the proximal face of disc 52, and a central sleeve 56 is connected to each rib 54, so that piston rod 30 may pass through sleeve 56 while piston 34 is in sealing engagement with cylinder 24. The air conduit, which is not shown, passes through piston 34 and extends within the interior of piston rod 30.

Figure 4:
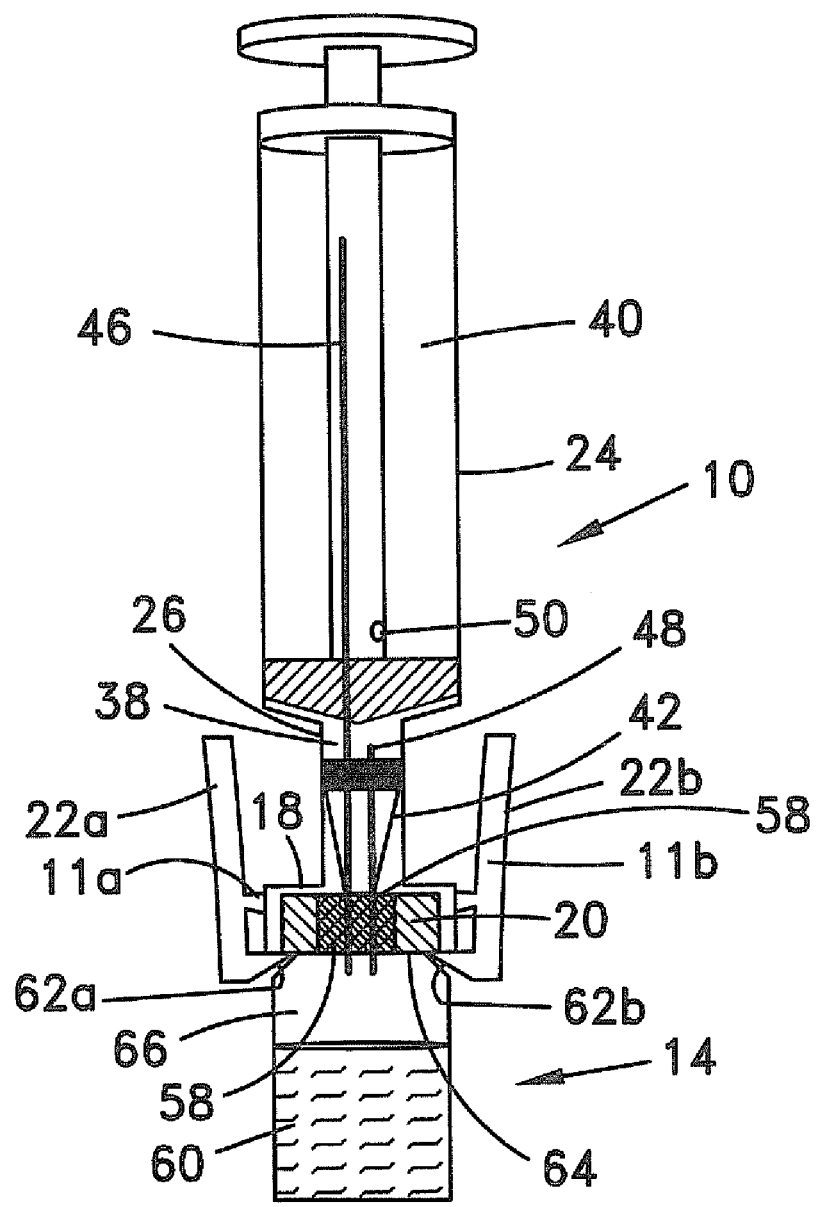
FIG. 4 is a schematic illustration, in vertical cross sectional view, of the releasable coupling of the apparatus of FIG. 1 with a drug vial.

FIG. 4 illustrates the coupling of transfer apparatus 10 to the head portion 20 of vial 14. Head portion 20 is provided with a central seal 58 (see FIG. 1), to prevent the outward leakage of hazardous drug 60 contained within vial 14.

Before transfer apparatus 10 and vial 14 are coupled, they are moved closed together. Locking elements 22a and 22b connected to the outer wall of collar 18 are flexed, to allow head portion 20 of vial 14 to enter collar 18. As head portion 20 of vial 14 is introduced within the cavity defined by collar 18, the distal end of membrane 42 is pressed against seal 58 in the head portion 20 of vial 14. Continued pushing of head 20 into collar 18 causes conical membrane 42 to collapse towards its base and conduits 46 and 48 penetrate both membrane 42 and seal 58 to establish fluid communication between the interior of vial 14 and air chamber 40 and liquid chamber 38 in transfer apparatus 10. When head portion 20 is pressed tightly into collar 18, the pointed ends 62a and 62b respectively of locking elements 22a and 22b engage distal edge 64 of head portion 20. This locks the transfer apparatus 10 firmly to head portion 20 and keeps membrane 42 tightly pressed against seal 58, thereby preventing contamination of the interior of the transfer apparatus and vial and also escape of the fluids within them to the surroundings.

When conduits 46 and 48 penetrate membrane 42 and seal 58 of vial 14, two alternate fluid passageways are formed. The first passageway is an air passageway defined by the interior of vial 14, air conduit 46, and air chamber 40. The second passageway is a liquid passageway defined by the interior of vial 14, liquid conduit 48 and liquid chamber 38. The interior of vial 14 which is not occupied by drug 60 may serve alternately as a passageway for air or for liquid, depending on which fluid occupies the proximal portion of the interior, as will be described hereinafter. Since the two fluid passageways are internal to transfer apparatus 10 and to vial 14, a liquid transfer operation between them is contamination-free.

As a safety measure a solid ring (not shown) may be attached to the distal end of transfer apparatus 10 fitting around conical membrane 42 by use of locking elements 22a and 22b. When the locking elements are engaged with the ring, compression of conical membrane 42 is prevented. Thus conduits 46 and 48 are also prevented from penetrating membrane 42, thereby avoiding exposure of the ends of the conduits to the surroundings and injury to a user. When the solid ring is removed, conical membrane 42 is able to be compressed and transfer apparatus 10 is able to be coupled to head portion 20 of vial 14, as described hereinabove.

The initial pressure of air within air chamber 40 and of air, or any other gas retained within interior space 60 of vial 14, may be slightly greater or less than atmospheric pressure. Although there may be an initial pressure difference between the air in air chamber 40 and the gas in the interior 66 of vial 14, upon penetration of membrane 42 and seal 58, the pressure within the air passageway quickly achieves equilibrium. During this stage, liquid conduit 48 is also in communication with the air which occupies the proximal portion of interior 66 of vial 14, and therefore liquid chamber 38 of transfer apparatus is also substantially at the same uniform pressure.

Figure 5:
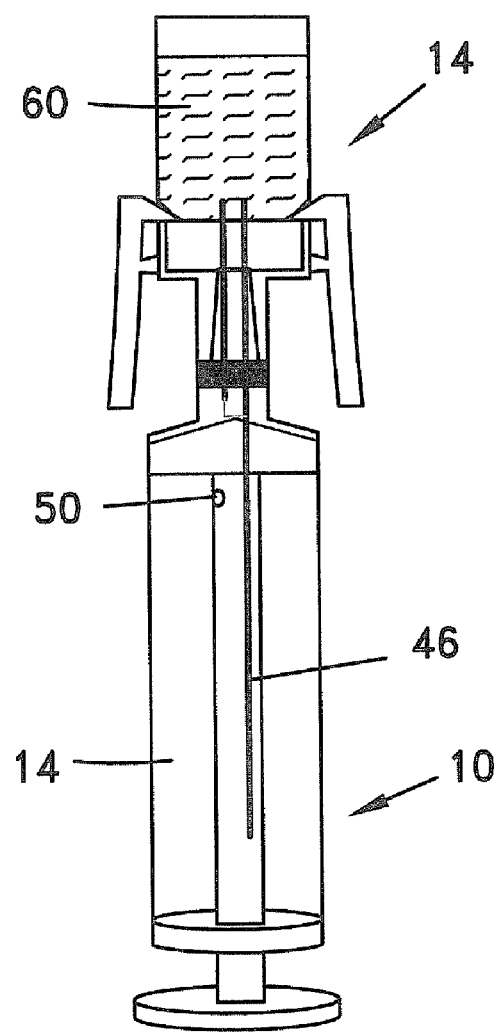
FIG. 5 is a schematic illustration, in vertical cross sectional view, of an inverted vial coupled with a liquid transfer device, prior to contamination-free fluid exchange.

As shown in FIG. 5, the coupled transfer apparatus 10 and vial 16 are then inverted, to enable the two-way fluid exchange of liquid drug from vial 14 to transfer apparatus 10 and simultaneously of air from transfer apparatus 10 to vial 14. Since vial 14 is inverted, drug 60 descends by gravity and occupies the proximal portion of vial 14. Since the pressure of air in chamber 40 is substantially equal to the pressure on the drug 60, drug 60 will be prevented from flowing through air conduit 46 and liquid conduit 48.

Figure 6:
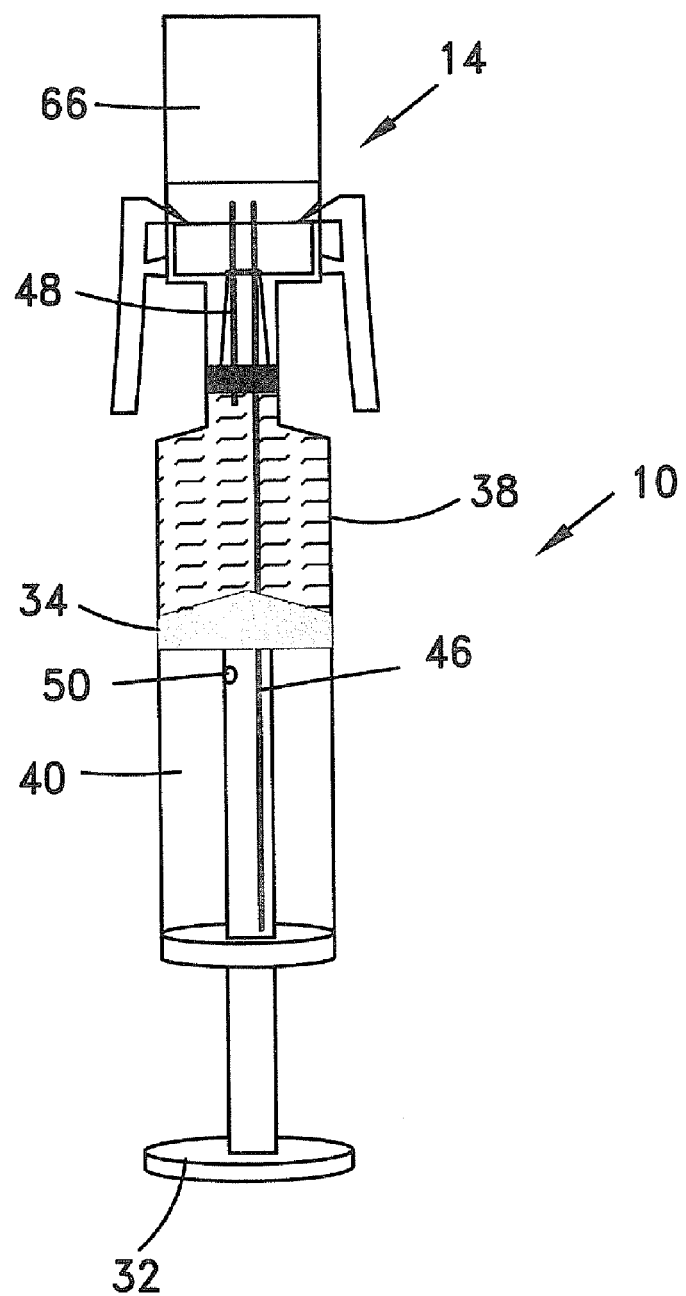
FIG. 6 is a schematic illustration of the transfer of a hazardous drug to a liquid chamber of the apparatus of FIG. 4.

The liquid passageway is shown in FIG. 6. When piston rod cap 32 is proximally displaced, the volume of liquid chamber 38 is increased, causing the liquid drug to be drawn by suction from vial 14 through conduit 48 into liquid chamber 38 within transfer apparatus 10. The entire amount of the drug in the vial, or any desired portion thereof, may be transferred to liquid chamber 38. As the piston is pulled proximally to cause liquid to be transferred from vial 14, the volume of air chamber 40 simultaneously is reduced, causing the air within chamber 40 to flow through conduit 46 to interior 66 of vial 14. The air flowing into vial 14 occupies the volume of the liquid that has been transferred out. The air will continue to flow through conduit 46 into the vial until the piston stops moving and the pressure within air chamber 40 and interior of vial 14 again reaches equilibrium.

After the desired amount of drug is transferred to liquid chamber 38, with reference again to FIG. 4, locking elements 22a and 22b are released from head portion 20 of vial 14. Transfer apparatus 10 is then separated from vial 14 by another axial motion, i.e. by being pulled axially apart. When the vial separates from the transfer device, conduits 46 and 48 are pulled through seal 58 of vial 40 and membrane 42 in the distal end of the transfer apparatus 10. As this happens, distal ends 46a and 48a (FIG. 2) of conduits 46 and 48, respectively, are wiped clean by seal 58. Any residual droplets of hazardous drug 60 are removed from the conduits and remain on the inner surface of seal 58 within the interior of vial 14, and therefore are not exposed to the ambient air. Membrane 42, at the same time, returns to the original position shown in FIG.

2; thereby sealing the air contaminated by contact with the drug inside air chamber 40 and the drug within liquid chamber 38.

Figure 7:
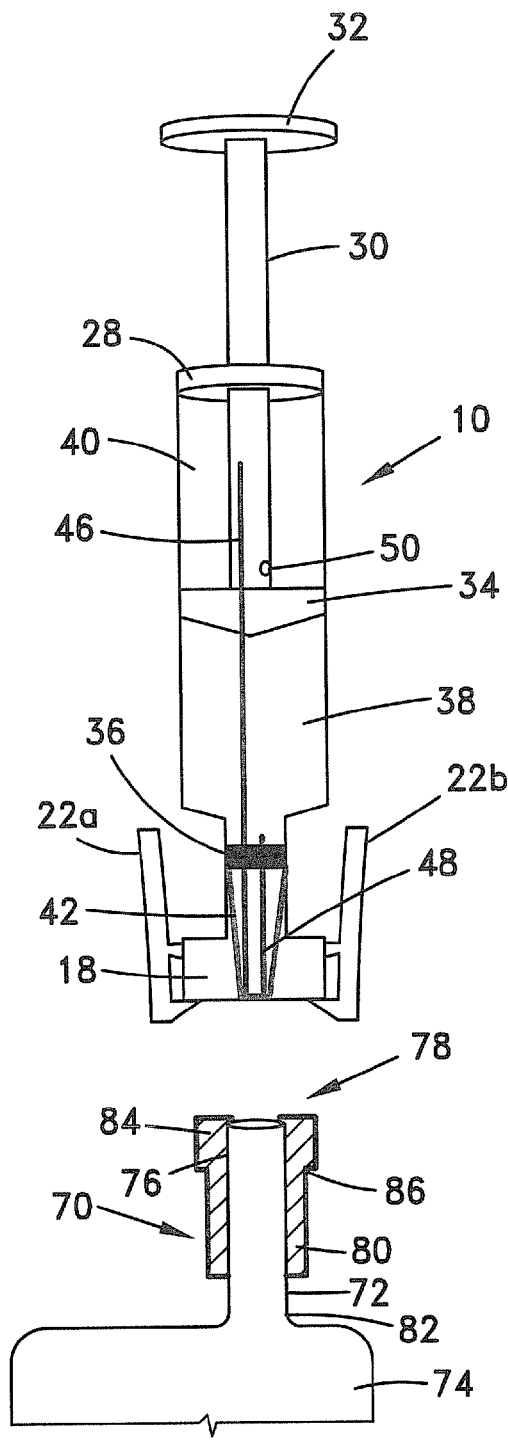
FIG. 7 schematically illustrates the transfer of the hazardous drug from the transfer apparatus of FIG. 2 to an IV bag.

FIG. 7 schematically illustrates the transfer of the hazardous drug from transfer apparatus 10 to an IV bag 74. Adaptor 70 is first attached to port 72 of an IV bag. The IV bag may be provided with a rubber seal 76, which prevents leakage of liquid from the IV bag. Adaptor 70 is configured with a central bore 78, in which port 72 is inserted, and a plurality of fins 80 lying in planes that pass through the bore axis. As adaptor 70 is mounted about inlet port 78, fins 80 contact outer wall 82 of inlet port 72 by a press fit. Adaptor 70 is also provided with a head portion 84, which has substantially the same shape and dimensions as head portion 20 of vial 14 (FIG. 2).

The IV bag is inverted such that it is below adaptor 70. In this orientation, the gaseous medium retained within the IV bag, e.g. air, is above the liquid. Transfer apparatus 10 is then coupled to adaptor 70 by pushing head portion 84 of adaptor 70 into collar 18 at the distal end of transfer apparatus 10. As head portion 84 of adaptor 70 is introduced within the cavity defined by collar 18, the distal end of membrane 42 is pressed against rubber seal 76 in the neck of port 72 of IV bag 74. Continued pushing of head 84 into collar 18 causes conical membrane 42 to collapse towards its base and conduits 46 and 48 penetrate both membrane 42 and seal 76 to establish fluid communication between the interior of IV bag 74 and air chamber 40 and liquid chamber 38 in transfer apparatus 10. When head portion 84 is pressed tightly into collar 18, the pointed ends of locking elements 22a and 22b engage distal edge 86 of head portion 84. This locks the transfer apparatus 10 firmly to adaptor 84 and keeps membrane 42 tightly pressed against seal 76, thereby preventing contamination of the interior of the transfer apparatus and IV bag and also escape of the fluids within them to the surroundings. After transfer apparatus 10 is coupled to adaptor 70, the user applies a distal force to rod cap 32. Piston 34 is therefore caused to be distally displaced towards separating element 3. As the piston moves the hazardous drug contained in the liquid chamber 38 of transfer apparatus 10 is pushed through port 72 into the IV bag. Simultaneously as the liquid drug is transferred to the IV bag, the volume of air chamber 40 is increased, causing the gaseous medium retained in the IV bag, e.g. air, to be transferred by suction to air chamber 40. The air ceases to flow through conduit 46 when piston stops moving and the pressure within air chamber 40 and within the IV bag reaches equilibrium. After the required amount of the drug is discharged into the IV bag, The proximal ends of locking elements 22a and 22b are pressed inwards to release collar 18 from head portion 84 of adaptor 70. Transfer apparatus 10 is slowly pulled apart from adaptor 70. As this separation takes place, conduits 46 and 48 are pulled back through seal 51, which continues to serve as a fluid barrier to prevent leakage from IV bag 74, and through membrane 42, which returns to its conical shape isolating the interior of liquid transfer apparatus 10 from the surroundings.

Transfer apparatus 10 may also be used to draw a liquid from the IV bag. To do this, after collar 18 is coupled to adaptor 70, the IV bag is inverted such that it is above transfer apparatus 10. Then piston rod cap 32 is proximally displaced, thereby simultaneously transferring the desired liquid from the IV bag to the liquid chamber 38 and air from the air chamber 40 to the interior of the IV bag.

In another embodiment the adaptor may comprise a hollow double cannula spike element for piercing the seal in the port of the IV bag, with a secondary port similar to the port of the IV bag, to which the tubing of an infusion set can be connected, and with a port which has substantially the same shape and dimensions as head portion 20 of vial 14 (FIG. 2), to which the transfer apparatus 10 is then coupled.

Figure 8:
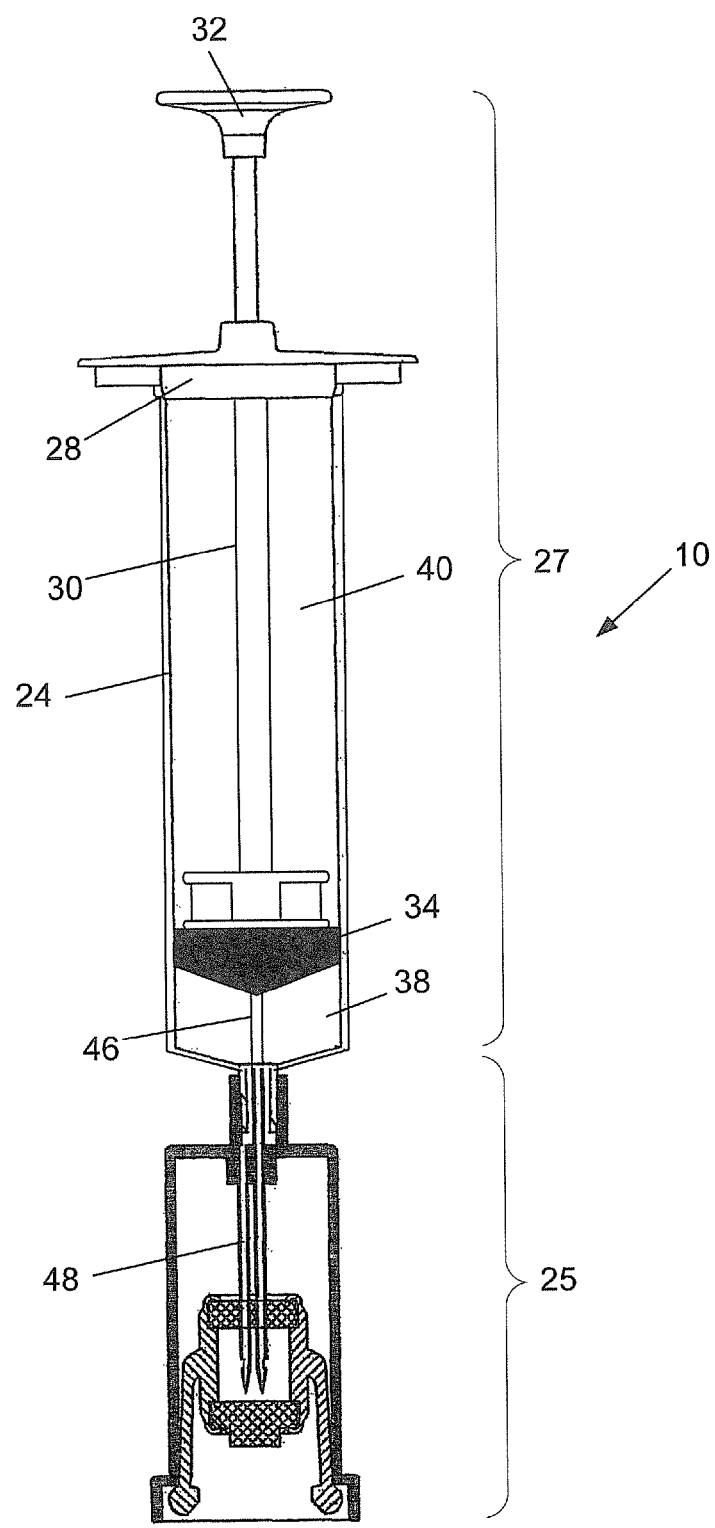
FIG. 8 is a vertical cross sectional of another embodiment of the contamination-free drug transfer apparatus of the invention.

FIG. 8 is a vertical cross sectional view of another embodiment of the contamination-free drug transfer apparatus 10 of the invention. In this embodiment of the invention, proximal section 27 of apparatus 10 is identical to that of the first embodiment described hereinabove.

Figure 9:
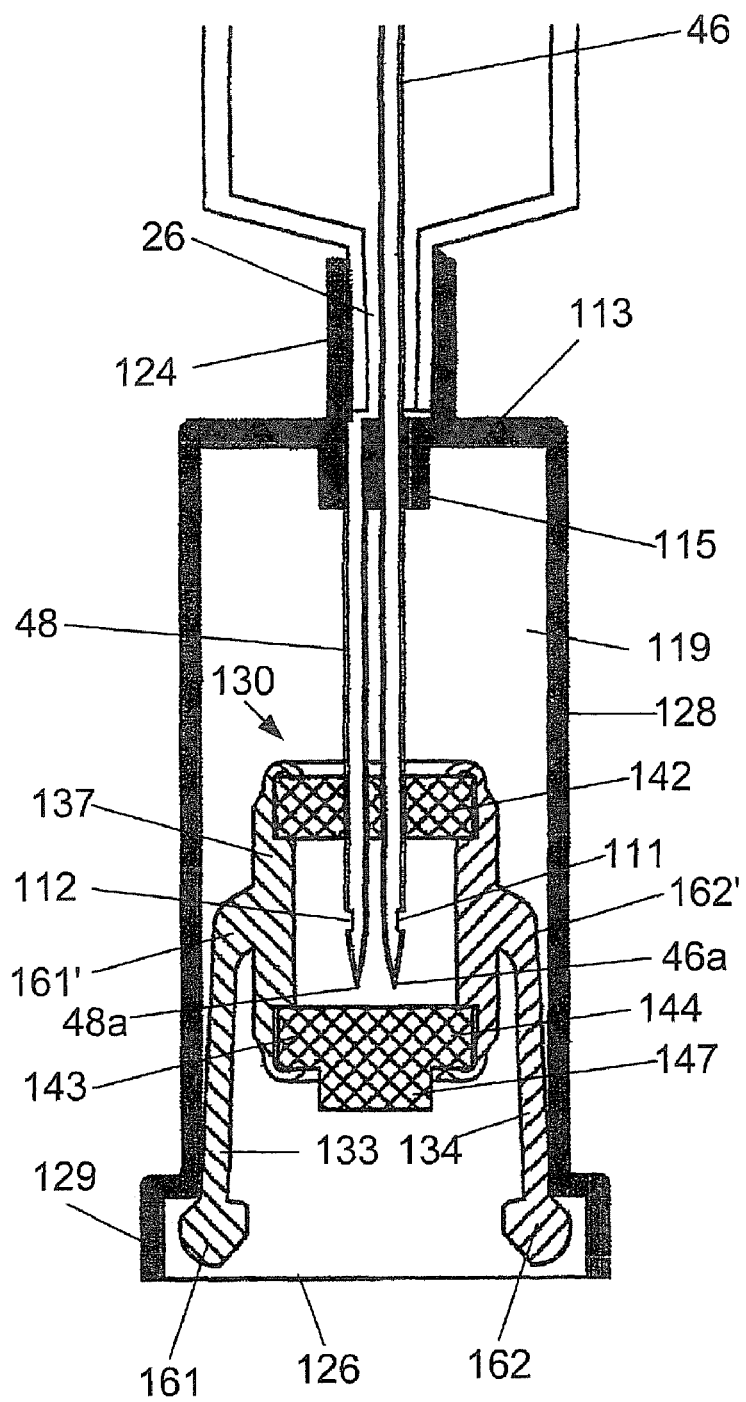
FIG. 9 is a cross sectional view of the connector section of the embodiment of the contamination-free drug transfer apparatus shown in FIG. 8.

As shown in FIG. 9, connector section 25 is connected to the throat 26 of proximal section 27 by means of a collar 124 which proximally protrudes from proximal cap 113 and surrounds throat 26. Throat 26 and collar 124 can be formed together as a single element at the time of manufacture, or permanently attached together, e.g. by means of glue or welding, or formed with a coupling means, such as threaded engagement or a luer connector. The connector section comprises a compressible and reciprocable double membrane seal actuator which assumes a normal, relaxed configuration by which the needles are concealed when the double membrane seal actuator is disposed in a first, distal position and which is compressed to expose the needles when proximally displaced. Connector section 25 is adapted to be releasably coupled to another fluid transfer component, which can be any fluids container with a standard connector such as a drug vial, intravenous bag, or an intravenous line to produce a "fluid transfer assembly", through which a fluid is transferred from one fluid transfer component to another.

As shown in FIG. 9, connector section 25 comprises a cylindrical, hollow outer body 128, a distal shoulder portion 129 radially protruding from body 128 and terminating with opening 126 through which the proximal end of a fluid transfer component is inserted for coupling, a double membrane seal actuator 130 reciprocably displaceable within the interior of body 128, resilient arms 133 and 134 which are connected at a proximal end thereof to an intermediate portion of cylindrical actuator casing 137, and stationary air conduit 46 and liquid conduit 48 that are retained in needle holder 115, which protrudes into interior 119 of connector section 25 from a central portion of closed proximal cap 113 thereof. Needle holder 115 is part of the outer body 128 and proximal cap 113 to which the needles are bonded.

Conduits 46 and 48 distally extend from needle holder 115, piercing membrane 142 of actuator 130. The distal ends of conduits 46 and 48 have sharp pointed ends 46a and 48a, respectively, and further provided with apertures 111 and 112, respectively, through which fluid is transferred during a fluid transfer operation. While the proximal end of air conduit 46 extends within the interior of fluid transfer unit 10, the proximal end of liquid conduit 48 terminates at or slightly proximally from cap 113 of connector section 25, so that the liquid conduit will be in fluid communication with the interior of throat 26 of fluid transfer unit 10.

As explained herein above, fluid is transferred by means of a pressure equalization arrangement in which the same volume of the hazardous drug and air are exchanged internally within the fluid transfer assembly. Fluid transfer unit 10 comprises a hollow piston rod 30 extending from cap 52 to piston 34, which sealingly engages the inner wall of, and is displaceable with respect to, barrel 24. Piston 34 defines two chambers of variable volume: a distal liquid chamber 38 between piston 34 and connector section 25 and a proximal air chamber 40 between piston 34 and stopper 28. Air conduit 46 passes through piston 34 and extends inside of hollow piston rod 30. Air flowing through conduit 46 enters the interior of piston rod 30 and exits to air chamber 40 through an aperture 50 (shown in FIG. 10C) formed at the distal end of piston rod 30. Conduit 48, which is considerably shorter than air conduit 46, is adapted to allow a solution of a drug to flow into liquid chamber 38.

Double membrane seal actuator 130 comprises a proximal disc shaped membrane 142 having a rectangular cross-section and a distal double disc shaped membrane 143 having a T-shaped cross-section with a rectangular proximal portion 144 and a distal portion 147 disposed radially inwards with respect to proximal portion 144. Membranes 142 and 143 are seated within casing 137, while distal portion 147 protrudes distally from casing 137. Arms 133 and 134 of equal length are elongated and are substantially longitudinally disposed, being attached at connection points 161' and 162', respectively, to casing 37. Arms 33 and 34 terminate with distal enlarged elements 161 and 162, respectively. The resilient arms 133 and 134 are designed such that, if not prevented from doing so, the distance between enlarged elements 161 and 162 is larger then the diameter of connector section 25. Enlarged elements 161 and 162 are configured to be received in, and engaged by, shoulder portion 129 when actuator 130 is disposed in a first, distal position. When actuator 130 is in this first position, pointed ends 46a and 48a are retained between membranes 142 and 143, preventing a user from being exposed to, and injured by, the pointed ends and also sealing the ends of conduits 46 and 48 from the surroundings, thereby preventing contamination of the interior of fluid transfer unit 10 and leakage of a harmful drug contained within the interior of unit 10 to the surroundings.

Figure 10:
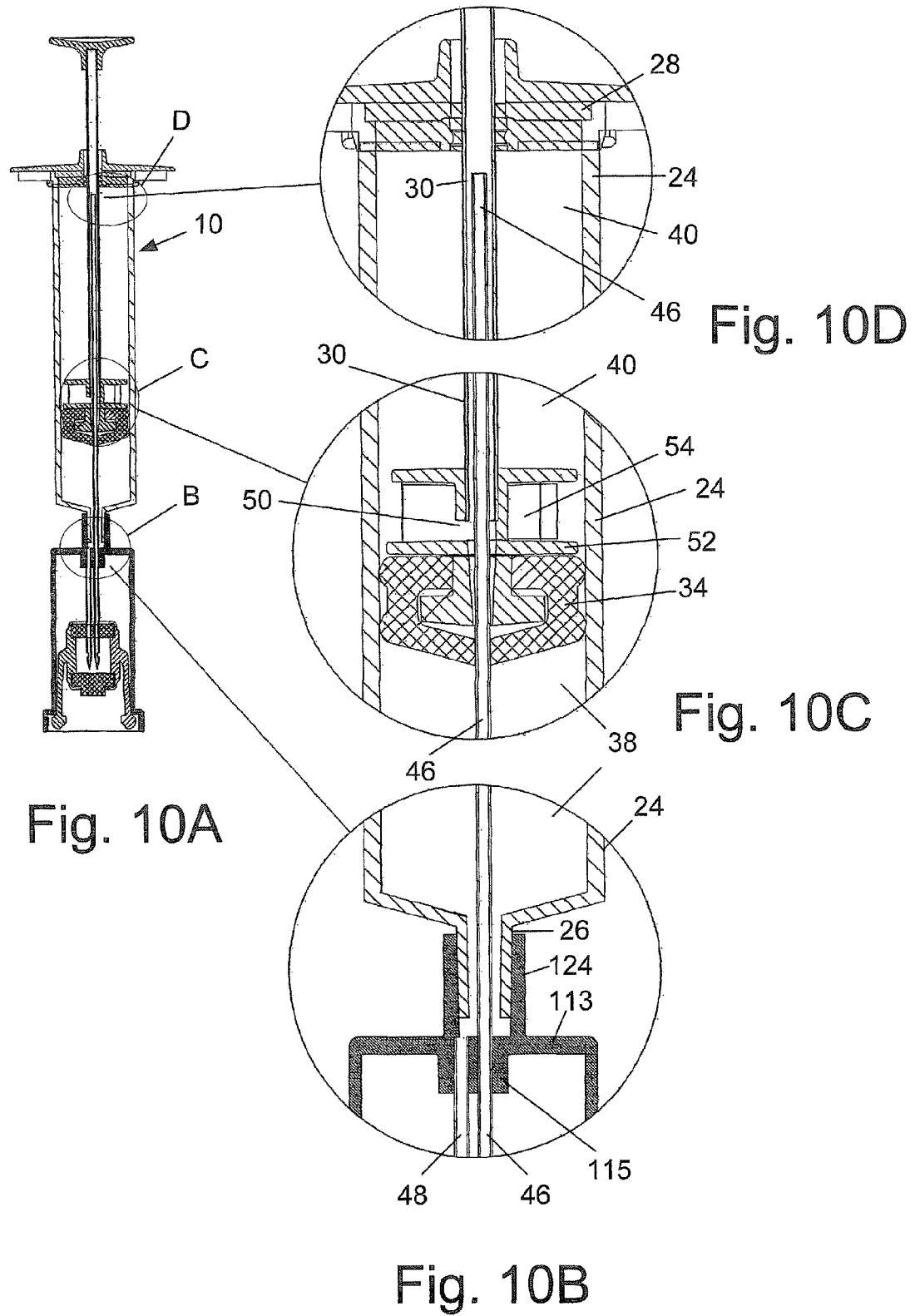
FIG. 10A is a cross sectional view of the fluid transfer apparatus and connector section shown in FIG. 7.
FIG. 10B, FIG. 10C, and FIG. 10D are enlarged views of sections of FIG. 10A illustrating the air and fluid passageways through the fluid transfer apparatus and connector section.

FIG. 10A is a cross sectional view of the fluid transfer apparatus 10 of the invention. FIG. 10B, FIG. 10C, and FIG. 10D are enlarged views of sections B, C, and D of FIG. 10A illustrating the air and fluid passageways through the fluid transfer apparatus. Referring to 10B, it can be seen how liquid conduit 48 passes through proximal cap 113 and the throat section 26 of the cylindrical wall 24 of transfer apparatus 10 and terminates inside distal liquid chamber 38. In FIG. 109C it is seen how the proximal end of the liquid chamber 38 is defined by the distal surface of piston 34. Air conduit 46 passes through liquid chamber 38 and can be seen in FIG. 10C passing through piston 34, disc 52, and reinforcing ribs 54 and entering the interior of hollow piston rod 30. Conduit 46 terminates near the top of cylindrical portion 24 of device 10. Air which enters at the distal end of conduit 46, can only exit at the distal end, where the air passes into the interior of hollow piston rod 30. Seen in FIG. 10C are one or more apertures 50 at the bottom of piston rod 30 that allow the air to enter proximal air chamber 40. As seen in FIG. 10B and 10C respectively, the distal end of air chamber 40 is defined by the proximal surface of piston 34 and its proximal end is defined by the distal surface of rubber stopper 28. It can be understood from FIG. 10A to FIG. 10D, that as the piston is moved, for example in the proximal direction, the volume of liquid chamber 38 increases and the volume of air chamber 40 decreases by the same amount. It is noted that rubber stopper 28 and piston 34 of transfer unit 10 and membranes 142 and 143 of connector section 25 are conventional self-sealing types that allow piston rod 30, air conduit 46 and liquid conduit 48 to slide through them, while maintaining a fluid seal isolating the interior of the volume closed by the stopper, piston, or membrane respectively from the outside.

Figure 11:
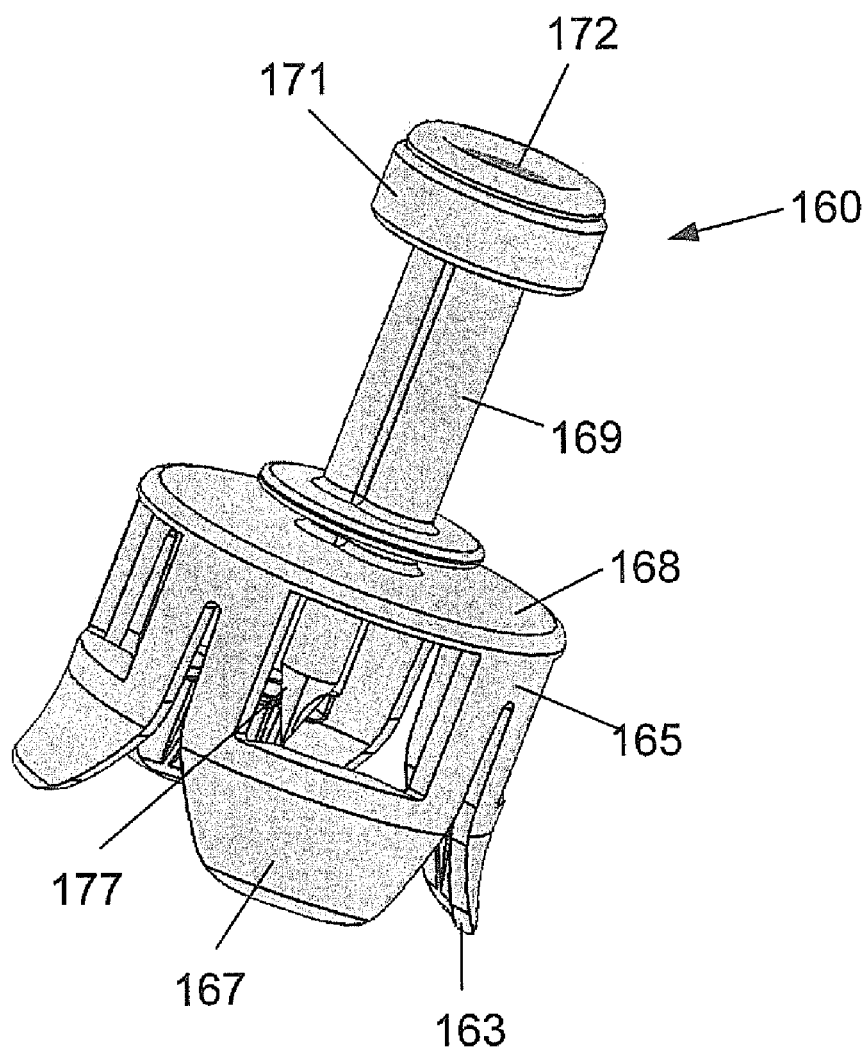
FIG. 11 is a perspective view of a vial adaptor to which a connector section can be connected.
Figure 12:
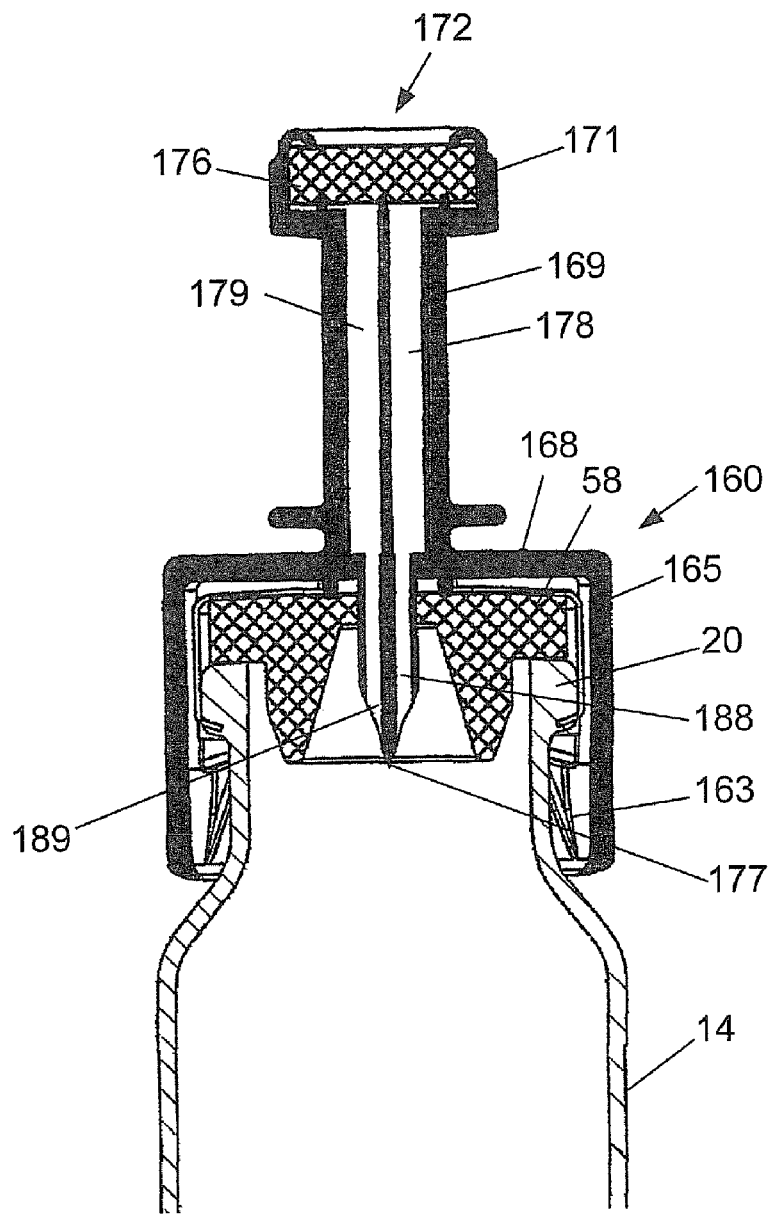
FIG. 12 is a vertical cross sectional view of a vial adaptor.

FIG. 11 and FIG. 12 show respectively a perspective view and a cross sectional view of vial adaptor 160. Vial adaptor 160 is an intermediate connection that is used to connect connector section 25 to a drug vial 14 or any other component having a suitably shaped and dimensioned port. Vial adaptor 160 can also be used with the first embodiment of the fluid transfer device. One of the main reasons for introducing a vial adaptor is that the top external surface of the membrane 58 that seals the top of commercially available drug vials are typically not smooth. Therefore the vial connector is used to provide a smooth seal to seal contact with the distal portion 147 of membrane 143 at the distal end of connector section 25 that is necessary to provide contamination-free transfer of the drug. Additionally, the material of which the membrane 58 is typically made has poor performance, i.e. when it is pierced by needles, it disintegrates and leaks after being punctured several times.

Vial adaptor 160 comprises a collar portion 165 provided with an annular proximal cap 168 and a longitudinal extension 169 projecting proximally from cap 168. Longitudinal extension 169 is a second reason for using the vial adaptor. It is much longer than the neck on a conventional drug vial and therefore fits into opening 126 at the distal end of connector section 25 to allow transfer of the drug as described hereinbelow. Collar portion 165 consists of a plurality of circumferential segments 167 formed with a convex lip 163 on the inner face thereof, for facilitating securement to a head portion 20 of a vial 14. Longitudinal extension 169 terminates proximally with a membrane enclosure 171 having a diameter larger than that of extension 169. Membrane enclosure 171 has a proximal central opening 172, by which membrane 176 retained therein is made accessible.

Two longitudinal channels 178 and 179 distally extending from membrane 176 are internally formed within longitudinal extension 169, and are adapted to receive conduits 46 and 48, respectively. On membrane enclosure 171 there is a slot and on the inner side of cylindrical, hollow outer body 128 of connector section 25 there is a ridge or pin (neither slot nor ridge are shown in the figures). During the connection the ridge/pin must enter and slide in the slot, in any other orientation the ridge/pin will contact membrane enclosure 171 and will prohibit further connecting movement. The ridge/pin and slot are located on their respective parts so that the conduits 46 and 48 will always enter their designated channel within the longitudinal extension 169. Longitudinal extension 169 terminates distally with a spike element 177 which protrudes distally from cap 68. Spike element 77 is formed with openings 188 and 189 in communication with channels 178 and 179, respectively.

Vial 14 has a central, proximal seal 58, which is adapted to prevent the outward leakage of a drug contained therein. When a distal force is applied to vial adaptor 160, the spike element pierces seal 58 of vial 14, to allow channels 178 and 179 to communicate with the interior of drug vial 14. When this occurs, circumferential segments 167 of the collar portion 165 are securely engaged with head portion 20 of vial 14. After membrane 58 of vial 14 is pierced it seals around spike 177 preventing the outward leakage of the drug from the vial. At the same time the tops of channels 178 and 179 are sealed by membrane 176, preventing air from entering or drug from exiting the interior of vial 14.

FIG. 13 to FIG. 16 illustrate, respectively, the secured double membrane engagement procedure made possible by actuator 30. As shown, distal membrane 143 of actuator 130 is brought into secured engagement with membrane 176 of vial adaptor 160, but it will be appreciated that the secured engagement operation can be carried in conjunction with any other suitable fluid transfer component. The procedure is carried out as follows: Step 1—Membrane enclosure 171 of vial adaptor 160 is positioned close to distal opening 126 of connector section 25. Step 2—A double membrane engagement procedure is initiated by distally displacing body 128 of connector section 25 until membrane enclosure 171 and extension 169 of vial adaptor 160 enters the distal end of the interior 119 of connector section 25. Step 3—Membrane 143 of actuator 30 is caused to contact and be pressed against the stationary membrane 176 of vial adaptor 160 by additional distal displacement of body 128. After the membranes are pressed tightly together the enlarged elements 161 and 162 are released from the shoulder portion 129. At this stage, membranes 143 and 176 are held pressed together by enlarged elements 161 and 162 and disengagement of actuator 130 from vial connector 160 by a relative proximal displacement is prevented. Step 4—Additional distal displacement of body 128 causes actuator 130 to move proximally relative to body 128 until the tips of conduits 46 and 48 pierce membranes 143 and 176 and are in fluid communication to the interior of vial 14. These four steps are performed by one continuous axial motion as connector section 25 is distally displaced relative to the vial adaptor 160, and they will be reversed to separate connector section 25 from vial adaptor 160 by holding connector section 25 stationary and displacing vial adaptor 160 distally. It is important to emphasize that the procedure is described herein as comprising four separate steps, however this is for ease in describing the procedure only. It is to be realized that in actual practice the secured double membrane engagement (and disengagement) procedure using the present invention is carried out using a single smooth axial movement.

Figure 13:
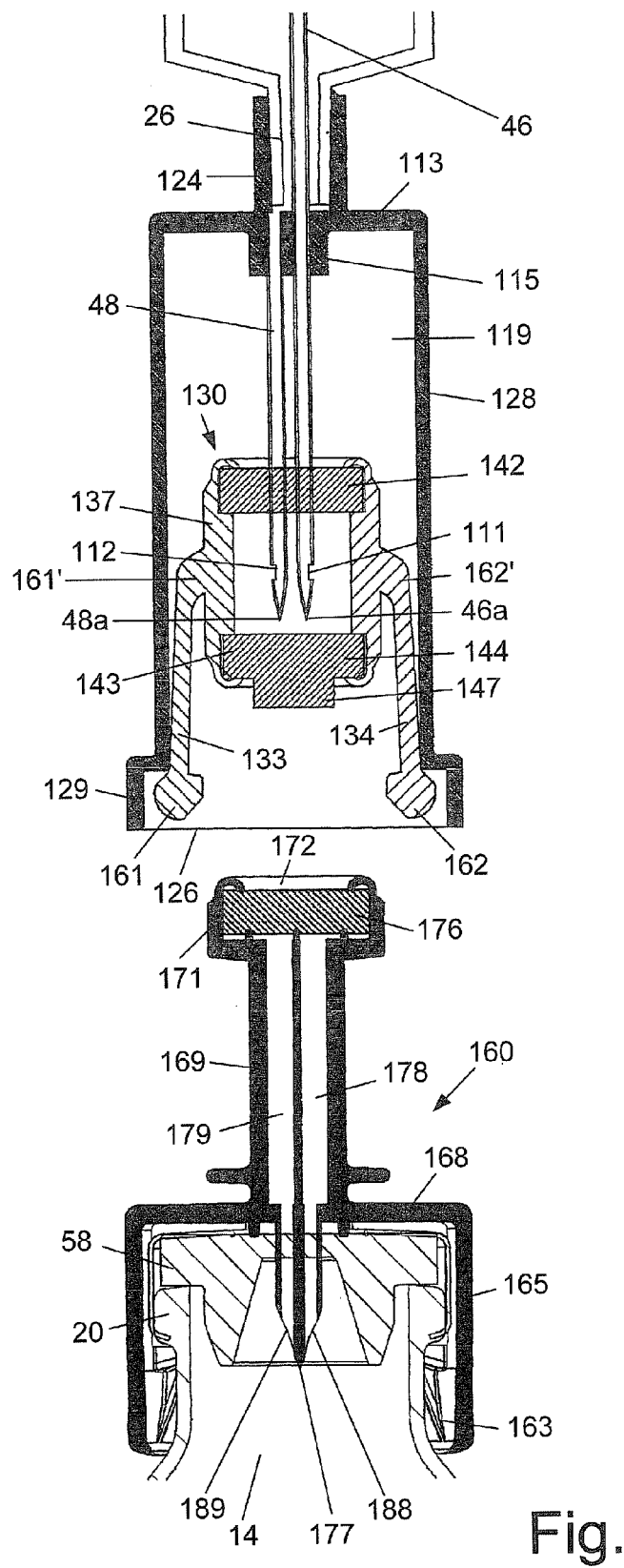
FIG. 13 to FIG. 16 are vertical cross sectional views of illustrating the secured double membrane engagement operation using the apparatus of FIG. 8.

The first step of the procedure of connecting the connector section 25, to which fluid transfer apparatus 10 is attached, to the vial adaptor 160, to which vial 14 is attached, is illustrated in FIG. 13. In the stage shown in FIG.

13, the double membrane seal actuator 130 in its first, distal position at the distal end of connector section 25 and brought close to the membrane enclosure 171 of vial adaptor 160. All of the elements of fluid transfer apparatus 10, connector section 25, vial adaptor 160, and vial 14 shown in FIG. 13 have been described hereinabove with reference to FIG. 9 and FIG. 12.

Figure 14:
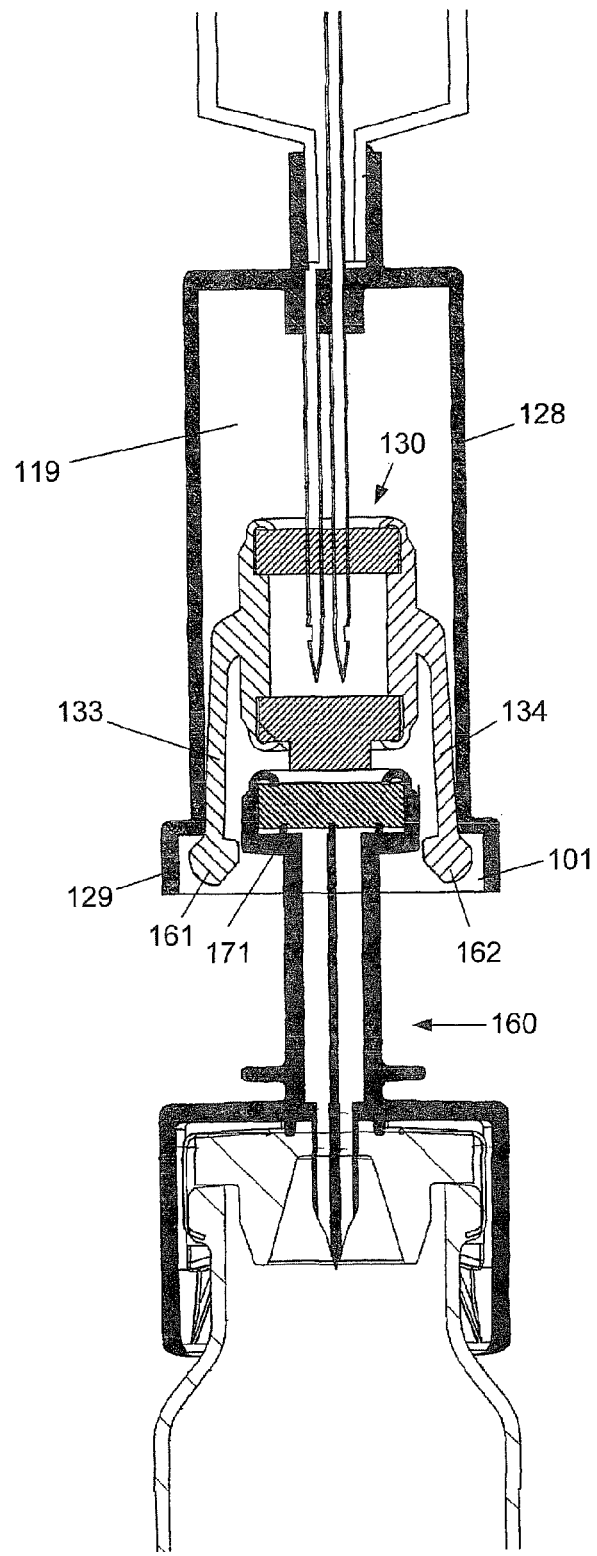

FIG. 14 illustrates the second step of the secured double membrane engagement procedure. The diameter of membrane enclosure 171 is less than the spacing between enlarged elements 161 and 162 when they are held in shoulder portion 129 by the natural tendency of the flexible arms 133 and 134 to push the enlarged portions laterally outward. This allows for effortless entry of membrane enclosure 171 into interior of 119. As connector section 25 is pushed in the direction of vial adaptor 160, enlarged elements 161 and 162 are held in shoulder portion 129 and prevented from moving inwards by the sides of membrane enclosure 171. Upper surfaces 131 and 132 of shoulder 129 are in contact with the distal portion of arms 133 and 134, respectively, and prevent them from being proximally displaced relative to body 128 of connector section 25.

Figure 15:
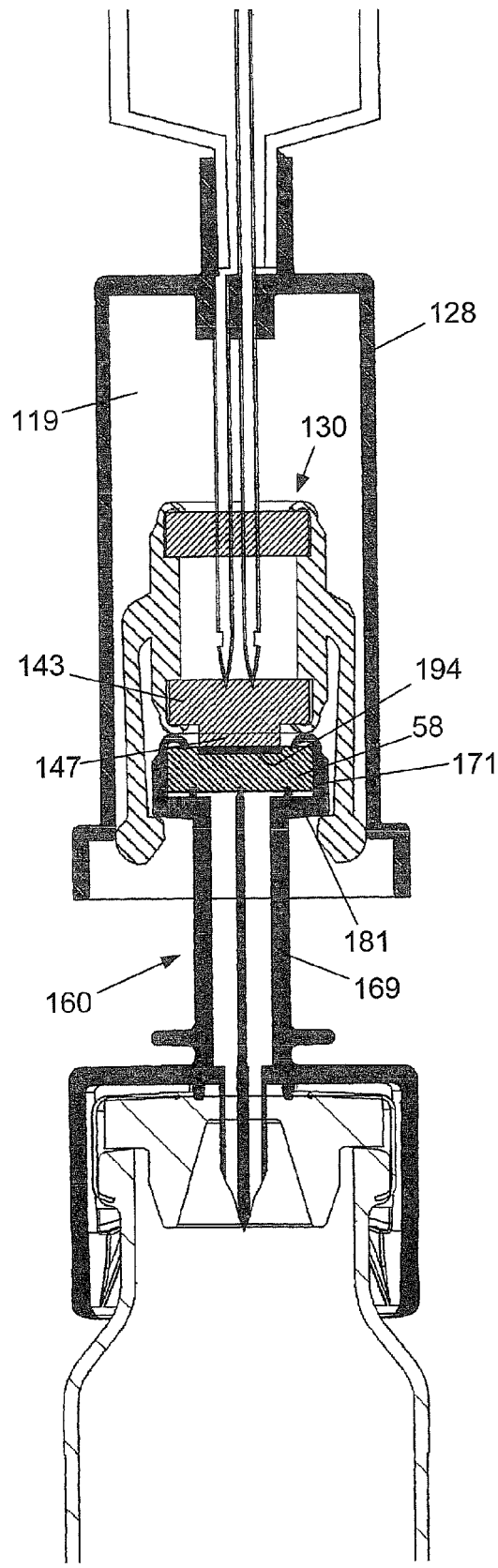
Figure 16:
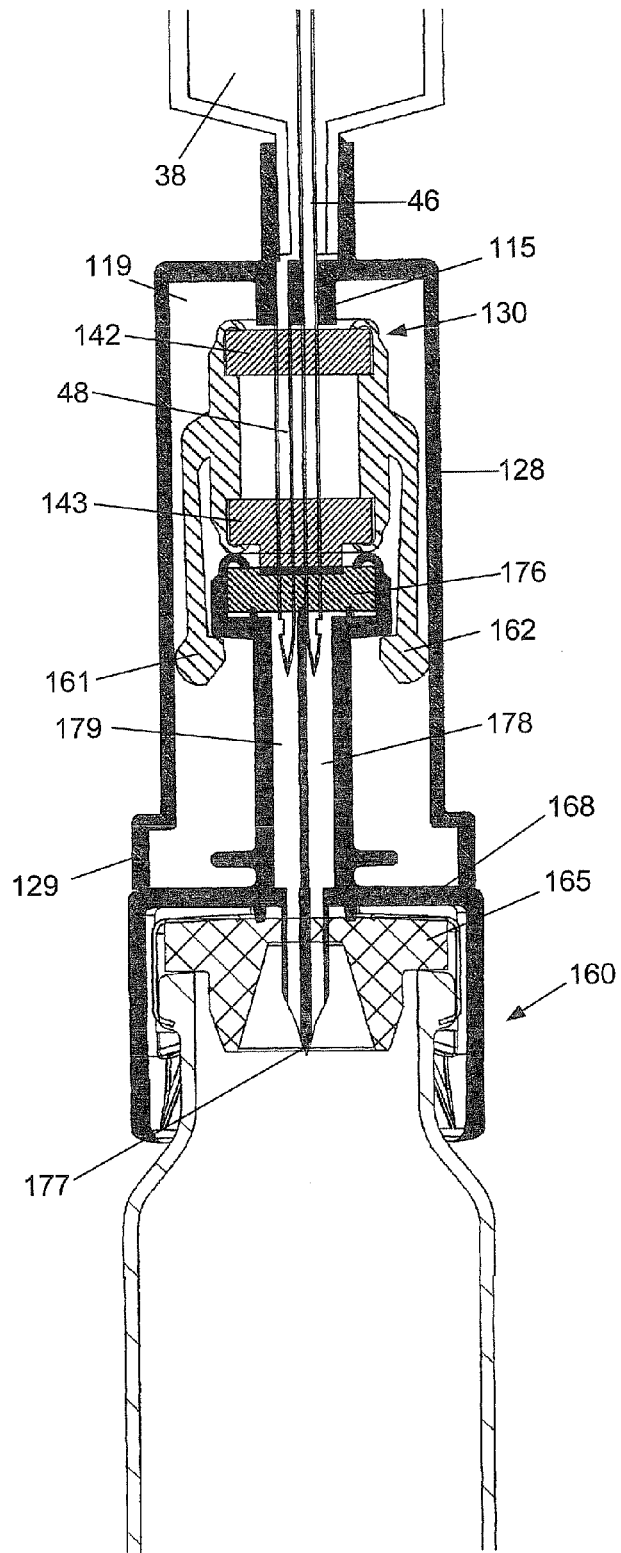

FIG. 15 illustrates the third step of the secured double membrane engagement procedure. Upon additional distal displacement of connector section 25, the distal membrane portion 147 of T-shaped membrane 143 enters central opening 172 (FIG. 11) of membrane enclosure 171. Distal membrane portion 147 contacts membrane 176 of the vial adaptor and the two membranes are compressed one against the other, as schematically represented by the dark area 194. While the membranes are being pressed together the actuator 130 is prevented from being able to ascend into the body 128 of connector 25 by the enlarged elements 161 and 162, which are prevented from coming out of the distal shoulder portion 129 the wall of the body 28 of connector 25 by the outer surface of membrane enclosure 171 of vial adaptor 60. As more force is applied to push connector section 25 and vial adaptor 160 together, the amount of compression of the membranes increases allowing the longitudinal extension 169 and membrane enclosure 171 to move further into the interior of 119 until the sides of membrane enclosure 171 have moved past the enlarged elements 61 and 62. Once they are no longer blocked by membrane enclosure, enlarged elements 161 and 162 are able to move radially inwards, are released from shoulder portion 129, and abut the distal underside 181 of membrane enclosure 171. At this stage, the two membranes 143 and 147 are locked together in secured and compressed engagement FIG. 16 illustrates the fourth step of the secured double membrane engagement procedure. Enlarged elements 161 and 162 have been released from shoulder portion 129 of connector section 25 and are prevented from moving laterally outwards by the interior wall of body 128 of the connector section. This keeps membrane enclosure 171 of the vial adaptor fixedly attached to the double seal actuator 130. Additional distal displacement of connector section 25 relative to vial adaptor 160 will cause double membrane seal actuator 130 and the attached vial connector 160 to move proximally within the interior 119 of connector section 25. Since conduits 46 and 48 are rigidly fixed in needle holder 115 at the proximal end of connector section 25, as double membrane seal actuator 130 moves proximally, the pointed distal ends 46a and 48a of conduits 46 and 48 will be progressively forced through diaphragms 143 and 176 until they enter longitudinal channels 178 and 179 in the vial connector 160. Since vial connector 160 had previously been connected to vial 14, spike 177 penetrates membrane 165 at the top of the vial 14 and therefore there now has been established two independent fluid passageways between the interior of the vial 14 and the distal liquid chamber 38 and proximal air chamber 40 in the fluid transfer apparatus 10 respectively.

As shown in FIG. 16, the proximal interior surface of enlarged elements 161 and 162 engage the planar underside of membrane enclosure 171 and are prevented from moving outwards; therefore membrane enclosure 171 is prevented from being inadvertently disengaged from the connector section under normal handling. However, if a relatively large magnitude vertical force is applied to the fluid transfer apparatus while the vial adaptor is held in a stationary position, the vial adaptor can be disengaged from the double membrane seal actuator, as will be described herein below.

Figure 17A:
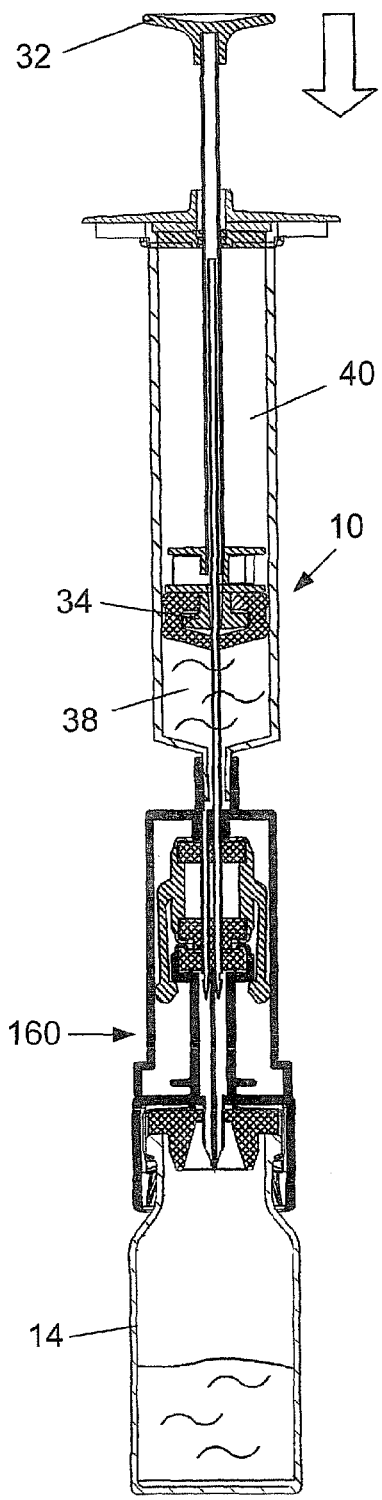
FIGS. 17A and 17B show schematically the two most common applications in drug preparation.
Figure 17B:
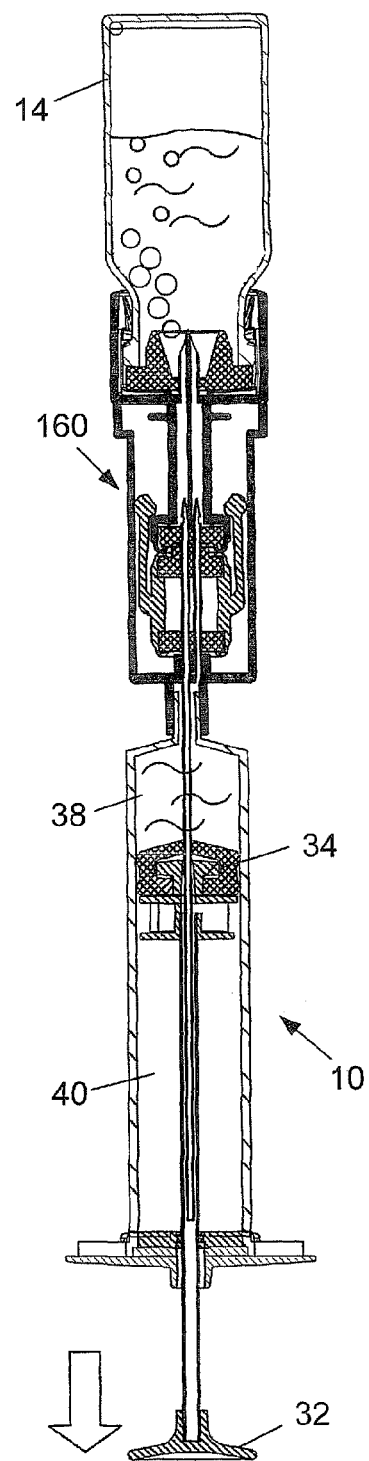

FIGS. 17A and 17B show schematically the two most common applications in drug preparation. FIG. 17A shows injection of a liquid into a vial and FIG. 17B shows withdrawal of liquid from a vial. In FIG. 17B are shown the air bubbles created by the air entering the vial from air chamber 40 through the air conduit. In a typical application the first stage of a process of administering a drug to a patient takes place in the pharmacy of a hospital. In a first step the pharmacist uses the secured double membrane engagement procedure described herein above to connect connector section 25 of apparatus 10 to vial adaptor 160, which has been previously connected to a vial 14 containing diluent (solvent), e.g. distilled water. At this stage piston 34 is in its most distal position and liquid chamber 38 is empty. Transfer apparatus 10 is now held as shown in FIG. 17B and the pharmacist fills the fluid chamber 38 of fluid transfer apparatus 10 with a measured quantity of diluent. The first vial is now disconnected from liquid transfer apparatus 10 and a second vial which contains drug in powder or concentrated liquid form is attached. At this stage, liquid chamber 38 of apparatus 10 is filled with diluent and the interior of vial 14 is partially filled with powder or liquid drug. Now, with the apparatus is held vertically with the vial at the bottom as shown in Fig, 17A. The pharmacist now pushes down on piston rod cap 32 forcing piston 34 distally and pushing the liquid out of liquid chamber 38 through conduit 48 and channel 179 (see FIG. 16) into vial 14. Simultaneously, as the volume of liquid chamber 38 is reduced by the distally moving piston, the volume of air chamber 40 is increased. This creates a temporary state of negative pressure in the air chamber and therefore air (or an inert gas) inside vial 14 will be sucked through channel 178 and conduit 46 into air chamber 40. Additionally and simultaneously, as the liquid is added to the vial, the volume available for the air in the vial is reduced creating a temporary state of positive pressure, therefore the air is forced from the vial 14 through channel 178 and conduit 46 into air chamber 40 which, as said, is in a temporary state of negative pressure. Once all of the liquid has been added to the vial, the apparatus is thoroughly shaken to completely dissolve the drug. After this, the pharmacist turns the apparatus over, as shown in FIG. 17B and pulls piston rod cap in the proximal direction to draw the required quantity of drug out of the vial and into the liquid chamber 38 of the transfer unit 10. The flow of liquid and air to simultaneously fill the liquid chamber and empty the air chamber is in the opposite directions to that described in relation to FIG. 17A.

Once the transfer unit 10 has been filled with the required quantity of drug, the pharmacist disengages the vial adaptor from the connector section of apparatus 10 and either injects the drug into an infusion bag through a dedicated adaptor or sends the transfer unit to the ward where the drug will be administered to the patient through a dedicated adaptor. To disconnect vial adaptor 160 from connector section 25 of fluid transfer apparatus 10 the four stages of the secured double membrane engagement procedure are performed continuously in reverse order. That is, vial adaptor 160 and connector section 25 are gripped firmly and an axial force is applied to pull them in opposite directions. This causes actuator 130 to be distally displaced within the interior 119 of connector section 25. Since outer surface of enlarged elements 161 and 162 are in contact with the inner wall surface of body 128 of the connector section, the double membrane seal actuator 130 and vial adaptor 160 move together towards the distal end of the connector section 25. Conduits 46 and 48 are firmly attached to needle holder 115 at the proximal end of the body 128 of the connector section. Therefore as seal actuator 130 moves distally within body 128 the distal ends 46a and 48a of conduits 46 and 48 will be progressively pulled back through diaphragms 143 and 176 until they are back in their original position between membranes 143 and 130. When actuator 130 reaches the distal end of the interior 119 of the connector section 25, the enlarged elements 161 and 162 are outwardly displaced by the natural tendency of the resilient arms 133 and 134 to push the enlarged portions laterally outward within shoulder portion 129. In this way the membrane enclosure 171 of the vial adaptor 160 is separated from the double membrane seal actuator 130.

Figure 18:
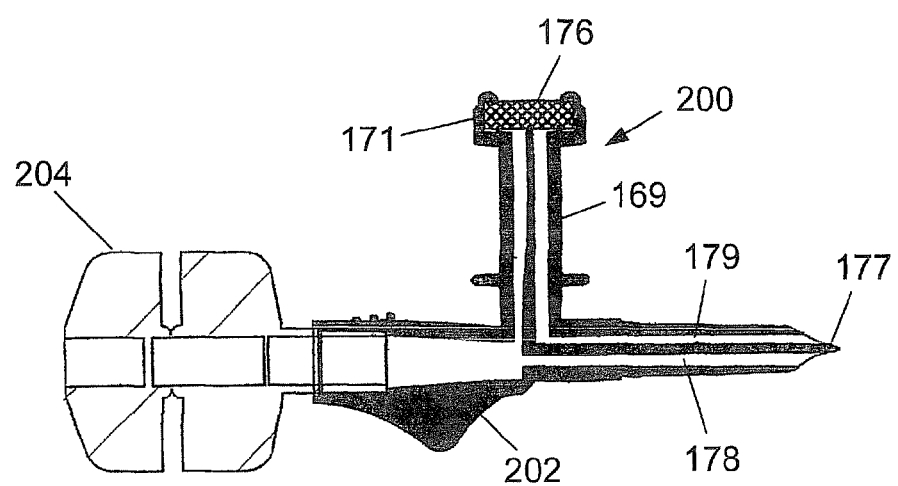
FIG. 18 is a cross sectional view showing a spike adapter used in conjunction with fluid transfer apparatus and connector section to transfer a drug to and from an intravenous (IV) bag.

FIG. 18 is a cross sectional view showing a spike adapter 200 used in conjunction with fluid transfer apparatus 10 to transfer a drug to and from an intravenous (IV) bag. Spike adaptor 200 comprises body 200 terminating in spike element 177 at the proximal end and a standard "twist off" end 204 to a spike port for connecting an infusion set at the distal end. Substantially at right angles to body 202 is a longitudinal extension 169. At the end of longitudinal extension 169 are membrane enclosure 171 and membrane 176. These elements are exactly as described hereinabove with respect to vial adaptor 60 of FIG. 11 including the presence of two separated channels 178 and 179 from the tip of spike element 177 to membrane 176.

Figure 19:
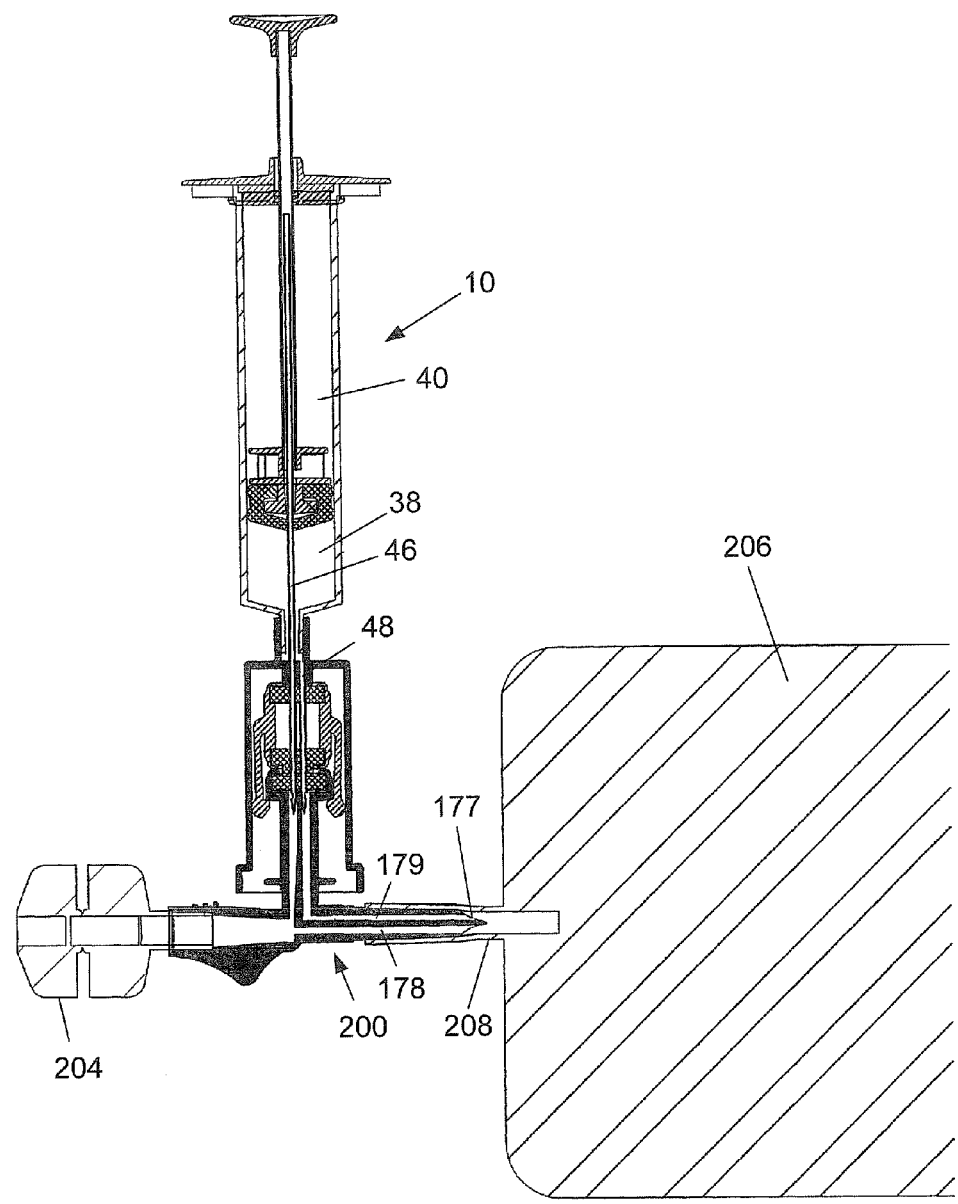
FIG. 19 is a cross sectional view showing a fluid transfer apparatus attached to infusion bag using the spike adaptor shown in FIG. 18.

FIG. 19 is a cross sectional view showing the fluid transfer apparatus 10 attached to infusion bag 206 using the spike adaptor shown in FIG. 18. Continuing with the scenario described above, spike element 177 is inserted into spike port 208 of infusion bag 206. The fluid transfer apparatus 10 filled with the drug connector section is connected to the spike adapter 200 using the secured double membrane engagement procedure described herein above. The bag is hung such that the liquid inside it is down and the part of the bag above the liquid, i.e. the volume of the bag occupied by air (or inert gas), is up and the tip of spike element 177 is located in this air and is surrounded by it. The piston in transfer apparatus 10 is then pushed in the distal direction pushing the drug out of the liquid chamber 38 in transfer apparatus 10, through liquid conduit 48 in connector section 25 and liquid channel 179 in spike adaptor 200 into infusion bag 206. Simultaneously, air from inside the infusion bag is drawn through liquid channel 178 in spike adaptor 200 and air conduit 46 into air chamber 40 in transfer apparatus 10. After the drug has been transferred to the infusion bag, the connector section 25 is disconnected from spike adapter 200, as described herein above, the twist-off end 204 is twisted off and infusion bag 206 is connected to an infusion tubing set and the drug is administered to the patient in the usual manner.

Spike adaptor 200 is also used to draw liquid from an IV bag in the same manner as described above for drawing a drug from a vial. In this case the IV bag is hung such that the spike element 177 is positioned at the bottom of the liquid and is surrounded by that liquid. Such liquid is typically used as a diluent for dissolving (reconstitution) of powder drugs in vials. It should be noted that injecting liquids through adaptor 200 into an infusion bag requires the presence of at least the same volume of air in the bag as the injected liquid in order to enable air/liquid exchange. The presence of such a quantity of air is not a default for all commercial bags; therefore, the required air can be prefilled by the pharmacist. In cases where the liquid is first withdrawn from the bag (for powder drug diluting in a vial), air from the air chamber 40 is injected into the bag, this way providing the required air for the next liquid injection into the IV bag. Although bag adaptor 200 is suited for liquid withdrawal and injection of liquid into an IV bag that contains a sufficient volume of gas; for the case when the IV bag does not contain a sufficient volume of gas, the drug injection adaptor 210, described herein below, is the better choice.

Figure 20:
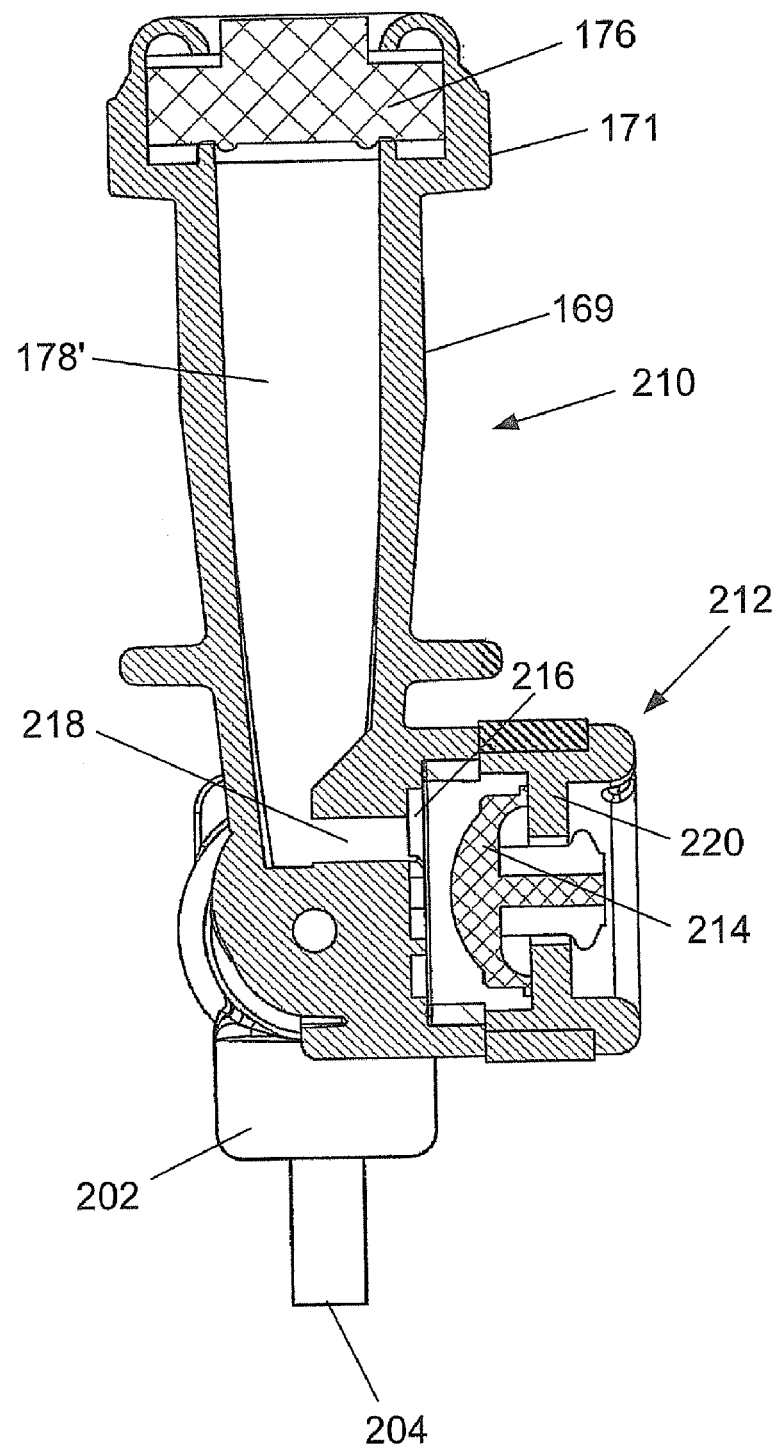
FIG. 20 is a cross sectional view showing a spike adapter comprising a one-way air inlet valve.
Figure 21:
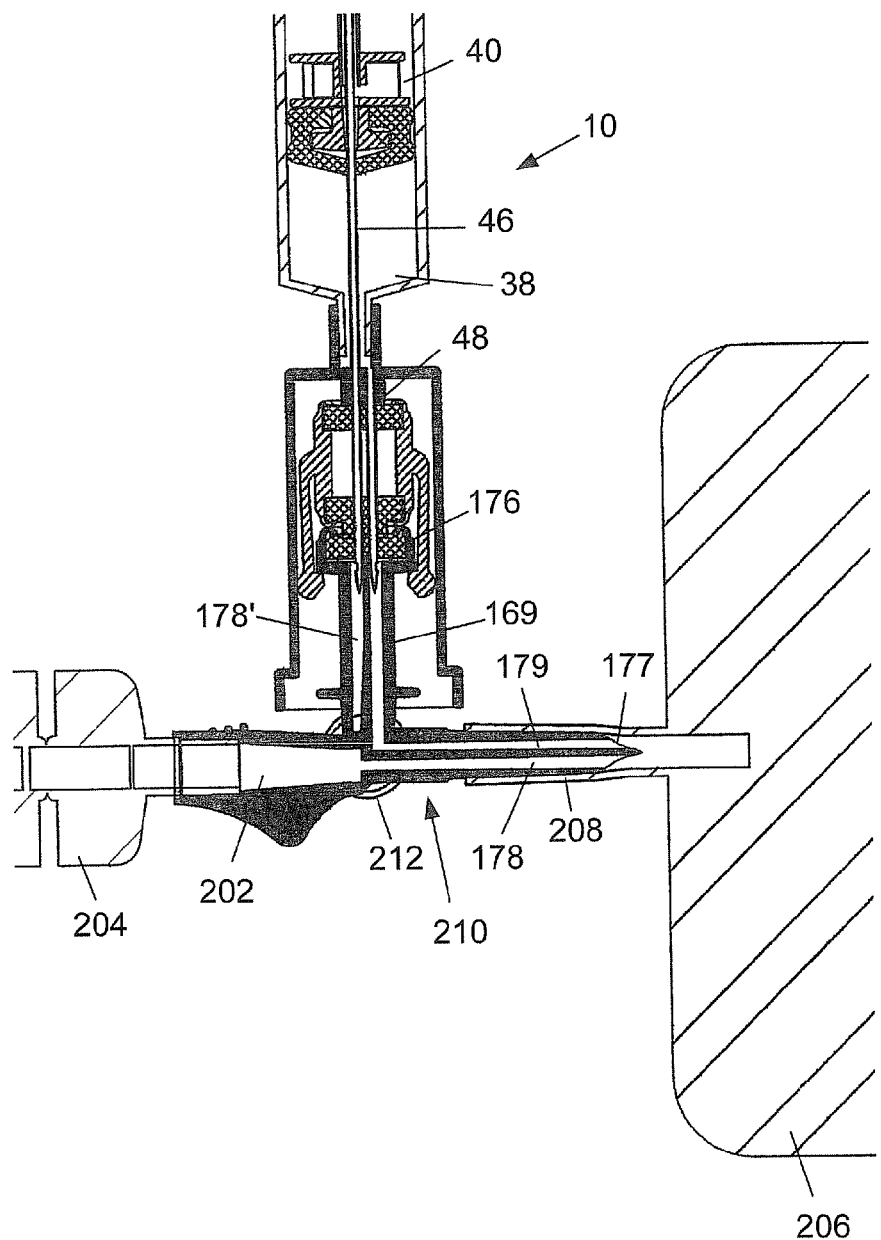
FIG. 21 is a cross sectional view showing a fluid transfer apparatus attached to infusion bag using the spike adaptor shown in FIG. 20.

FIG. 20 is a cross sectional view showing a spike adapter 210 comprising a one-way air inlet valve 212. FIG. 21 is a cross sectional view showing a fluid transfer apparatus attached to an infusion bag using the spike adaptor shown in FIG. 20. Most of the components of spike adaptor 210 are the same as those of spike adaptor 200 shown in FIG. 18 and FIG. 19. In addition to one-way valve 212 the other major difference between the two spike adaptors is that in spike adaptor 210 air channel 178 is not continuous from the tip of spike element 177 to diaphragm 176. The channel is blocked so that air can not pass between the interior of the IV bag and air chamber 40 in transfer apparatus 10. In spike adaptor 210 a channel 178' is provided in longitudinal extension 169. When the tip of air conduit 46 penetrates through diaphragm 176 it enters the proximal end of channel 178'. Air enters channel 178' through opening 218 from the one-way valve. The operation of one-way valve 212 is easily understood from FIG. 20. Inside the valve is dome shaped rubber cap 214. The center of the cap is attached to the frame of the adaptor and the circumference sits on a flat seat 220. When liquid is injected into IV bag 206 from liquid chamber 38, the volume of the air chamber 40 in transfer apparatus 10 is increased creating a temporary state of air negative pressure. Negative pressure on the side of the fluid transfer apparatus causes the cap 214 to "lift off" seat 220 allowing ambient air to be sucked in through the one way valve 212 and air to flow through hole 218 into channel 178'. In the absence of negative pressure or if there is a positive pressure on the side of the fluid transfer apparatus, then the cap 214 is pushed down onto seat 220 blocking the flow of air through valve 212. Adaptor 210 enables injection of liquids into the bag regardless of the bag/liquid/air position and it requires no presence of air in the IV bag. However, liquid can not be withdrawn from the IV bag using adaptor 210 since in order to draw liquid from the IV bag, the volume of the air chamber in apparatus 10 is reduced, thereby creating a positive pressure and closing valve 212. Note that while using adaptor 210 air can be sucked into transfer apparatus 10 but no air or drug or vapors can ever escape transfer apparatus 10, since for this to happen the pressure inside the air chamber of the transfer apparatus would have to be higher than that on the other side of valve 212, and therefore the one-way valve will be in its normally closed configuration. In order to insure sterility and prevent the entrance of bacteria into the fluid transfer apparatus, a standard 0.22 micron filter 216 is provided covering opening 218 into channel 178'. After the drug has been transferred to the infusion bag, the connector section 25 is disconnected from spike adapter 210, as described herein above, the twist-off end 204 is twisted off and infusion bag 206 is connected to an infusion tubing set and the drug is administered to the patient in the usual manner.

Figure 22:
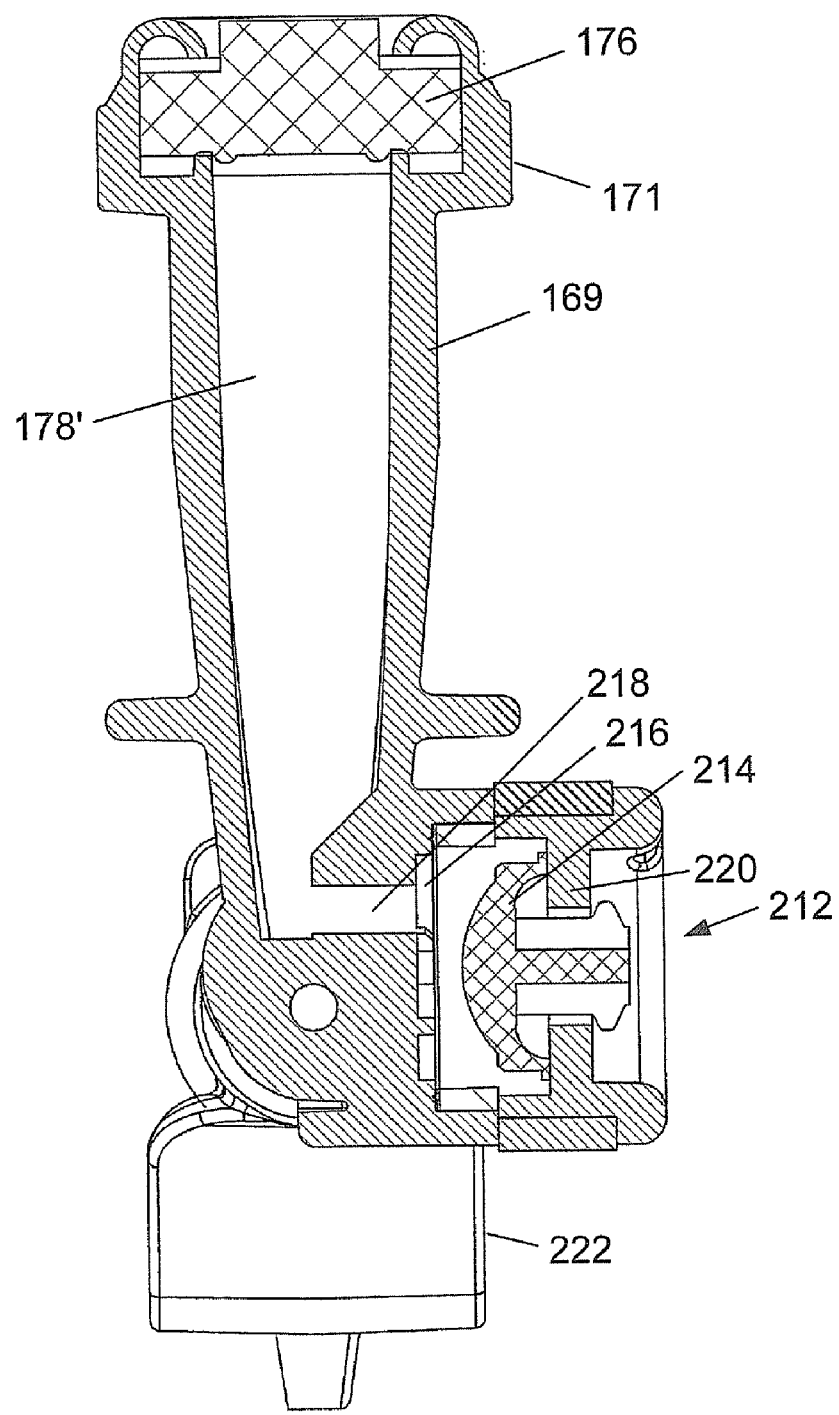
FIG. 22 is a cross sectional view showing an adapter for transferring a drug directly from a fluid transfer assembly of the invention directly into the bloodstream of a patient.
Figure 23:
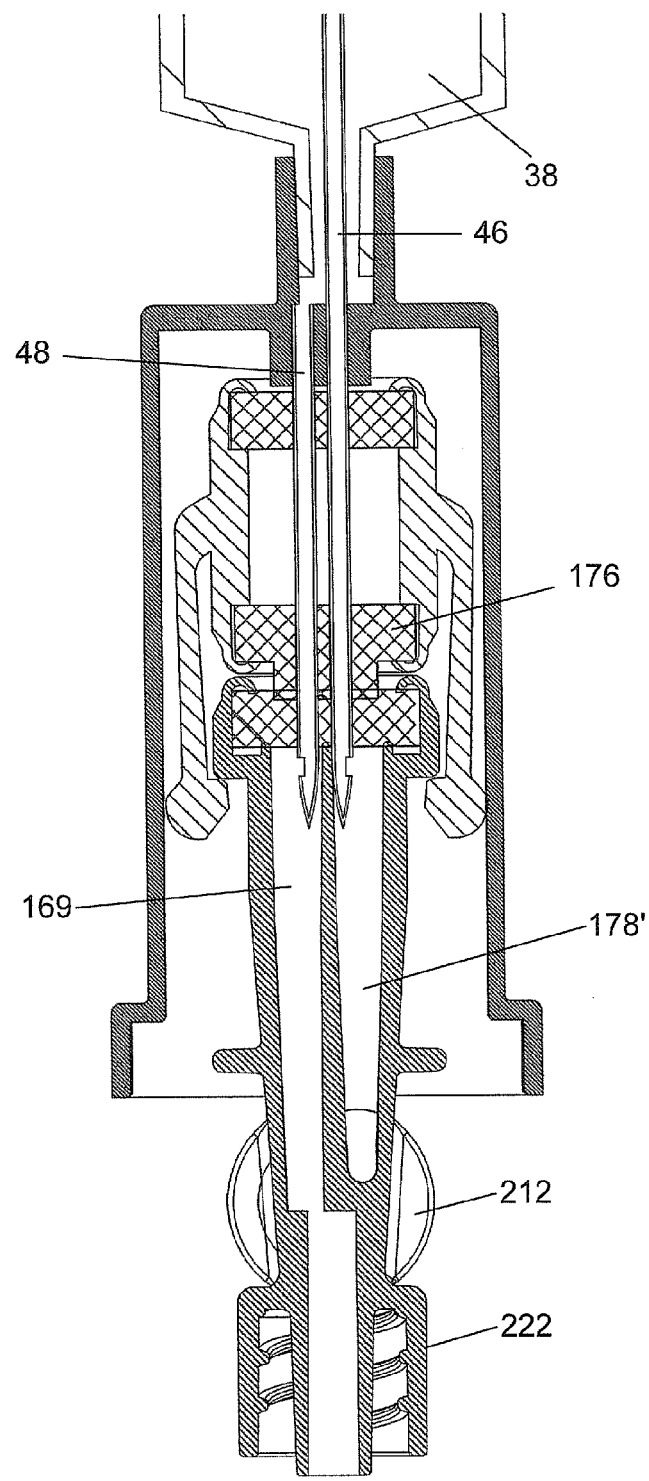
FIG. 23 is a cross sectional view showing a fluid transfer apparatus attached to the adapter of FIG. 22.

FIG. 22 is a cross sectional view showing an adapter 222 for transferring a drug directly from a fluid transfer assembly 10 of the invention into any fluids receiver which is equipped with a standard luer connector as a port, such as: infusion tubing leading directly to the bloodstream of a patient, tubing systems, receptacles, stopcocks, etc. Adapter 222 comprises a one-way air inlet valve 212 in order to provide the required volume of air in air chamber 40 of transfer apparatus 10 necessary to replace the volume of liquid that is expelled from the liquid chamber during injection of the liquid. FIG. 23 is a cross sectional view showing a fluid transfer apparatus 10 attached to adapter 222 via connector section 25. Adapter 222 is essentially the same as spike adapter 210 shown in FIG. 20, with the exception that spike element 177, body 202, and twist off end 204 are replaced by standard luer connector 222, which is adapted to be connected directly to any luer connector port.

It is noted that although the detailed description of the operation and use of fluid transfer apparatus 10, especially its use with the various adaptors, relates to the embodiment shown in FIG. 8, these various adaptors can also be attached to the connection section of the embodiment of apparatus 10 shown in FIG. 1 and used to transfer fluids in a similar manner.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

The invention claimed is:

1. A connector section for use in a fluid transfer operation, said connector section comprising a hollow cylindrical outer body having:
  (a) a distal shoulder portion radially protruding from said outer body and terminating with an opening through which a proximal end of a fluid transfer component can be inserted for coupling;
  (b) a closed proximal cap having a central portion comprising connection means protruding proximally from it to connect to a distal end of a fluid transfer apparatus;
  (c) a needle holder protruding into the interior of said outer body from the central portion of said closed proximal cap for retaining therein at least one conduit comprising a sharp pointed end and further provided with an aperture through which fluid is transferred during said fluid transfer operation; and
  (d) a double membrane seal actuator reciprocably displaceable within the hollow interior of said outer body;
  wherein said double membrane seal actuator comprises:
    (i) a cylindrical actuator casing;
    (ii) a proximal membrane that seals the proximal end of said casing;
    (iii) a distal membrane that seals the distal end of said casing, wherein a part of said distal membrane protrudes distally from said casing; and
    (iv) at least two resilient arms which are connected at a proximal end thereof to an intermediate portion of the exterior of said casing and comprise enlarged elements at their distal ends.

2. A connector section according to claim 1, wherein when the double membrane seal actuator is at the distal end of the cylindrical body of said connector section the enlarged elements of the resilient arms are pressed into the distal shoulder portion of the cylindrical body of said connector section, thereby allowing the membrane enclosure at the proximal end of the fluid transfer component to be inserted into the opening at the distal end of said connector section and advanced until said membrane in said membrane enclosure contacts the part of the distal membrane that protrudes distally from the casing of said double membrane seal actuator.

3. A connector section according to claim 2, wherein the diameter of the distal shoulder portion and the size of the enlarged elements at the distal end of the arms are such that, when an axial force is applied to push the double membrane seal actuator and fluid transfer component towards each other, the sides of the membrane enclosure prevent said enlarged elements at the distal end of the arms from moving radially inwards thereby causing the distal actuator membrane to be compressed against the membrane in said membrane enclosure until the sides of said membrane enclosure are displaced proximally in relation to said enlarged elements; at which point said enlarged elements have room to move radially inwards, are released from the distal shoulder portion of said double membrane seal actuator, and abut the distal underside of said membrane enclosure; thereby locking said distal actuator membrane against said membrane in said membrane enclosure in secured and compressed engagement, preventing disengagement of said actuator from said fluid transfer component, and allowing said actuator and said coupled fluid transfer component to be reciprocably displaced within the hollow interior of the outer body of said connector section.

4. A connector section according to claim 1, wherein when the double membrane seal actuator is at the distal end of the cylindrical body of said conductor section, the sharp pointed end of the at least one conduit are located between the proximal membrane and the distal membrane of said double membrane seal actuator.

5. A connector section according to claim 3, wherein the distance that the actuator and attached fluid transfer component can be displaced proximally within the hollow interior of the outer body of said connector section and the length of the at least one conduit are such that, when said actuator and said attached fluid transfer component are displaced proximally, the sharp pointed end of said at least one conduit penetrates the distal membrane of said actuator and the membrane in the membrane enclosure, thereby establishing a fluid path between said connector section and said fluid transfer component; and, when said actuator and attached fluid transfer component are displaced distally within said hollow interior of said outer body of said connector section, said sharp pointed end of said at least one conduit is pulled back through said distal membrane of said actuator and said membrane in said membrane enclosure, thereby breaking the fluid path between said connector section and said fluid transfer component.

6. A method for coupling the connector section of claim 1 to a fluid transfer component in order to affect a secured double membrane engagement, said method comprising the steps of:

(a) positioning the opening in the distal shoulder portion of the outer body of said connector section in the vicinity of the proximal end of said fluid transfer component;

(b) initiating a double membrane engagement operation by distally displacing the outer body of said connector section until a membrane enclosure at the proximal end of said fluid transfer component is received in the interior of said connector section;

(c) additionally displacing distally said outer body relative to said fluid transfer component until the distal membrane of said actuator contacts and is pressed against a membrane in said membrane enclosure at the proximal end of said fluid transfer component, wherein during this step the enlarged elements at the distal end of the arms attached to the double membrane seal actuator are held in the distal shoulder portion of said outer body of said connector section by the sides of said membrane enclosure, thereby preventing said actuator from moving proximally within said outer body of said connector section; and (d) additionally displacing distally said outer body relative to said fluid transfer component until said distal membrane of said actuator and said membrane in said membrane enclosure at the proximal end of said fluid transfer component are compressed together sufficiently to allow said sides of said membrane enclosure to pass said enlarged elements, allowing said arms to move radially inwards, thereby locking said distal actuator membrane against said membrane in said membrane enclosure in secured and compressed engagement, preventing disengagement of said actuator from said fluid transfer component, and allowing said actuator and said attached fluid transfer component to be reciprocably displaced within the hollow interior of the outer body of said connector section, whereupon when said actuator and attached fluid transfer component are displaced proximally within the hollow interior of said outer body of said connector section, the sharp pointed end of the at least one conduit penetrates the distal membrane of said actuator and the membrane in said membrane enclosure, thereby establishing a fluid path between said connector section and said fluid transfer component; and, when said actuator and attached fluid transfer component are displaced distally within said hollow interior of said outer body of said connector section, said sharp pointed end of said at least one conduit is pulled back through said distal membrane of said actuator and said membrane in said membrane enclosure, thereby breaking said fluid path between said connector section and said fluid transfer component.

7. A method according to claim 6 wherein the structure of the connector section enables the connector section and the fluid transfer component to be connected by a single axial motion and disconnected by a single axial motion without having to set a locking securing device or a release mechanism.

* * * * *